(12) United States Patent
Huang

(10) Patent No.: US 10,360,673 B2
(45) Date of Patent: Jul. 23, 2019

(54) IMAGE ANALYSIS

(71) Applicant: EyeKor, LLC, Madison, WI (US)

(72) Inventor: Yijun Huang, Fitchburg, WI (US)

(73) Assignee: EyeKor, LLC, Madison, WI (US)

( * ) Notice: Subject to any disclaimer, the term of this patent is extended or adjusted under 35 U.S.C. 154(b) by 137 days.

(21) Appl. No.: 15/072,046

(22) Filed: Mar. 16, 2016

(65) Prior Publication Data

US 2016/0284103 A1 Sep. 29, 2016

Related U.S. Application Data

(60) Provisional application No. 62/269,601, filed on Dec. 18, 2015, provisional application No. 62/138,485, filed on Mar. 26, 2015.

(51) Int. Cl.
  *A61B 5/00* (2006.01)
  *G06T 7/62* (2017.01)
  *G06T 7/00* (2017.01)

(52) U.S. Cl.
  CPC .......... *G06T 7/0012* (2013.01); *A61B 5/0066* (2013.01); *G06T 7/62* (2017.01); *G06T 2207/10101* (2013.01); *G06T 2207/20104* (2013.01); *G06T 2207/30041* (2013.01); *G06T 2207/30096* (2013.01)

(58) Field of Classification Search
  CPC ....... A61B 3/102; A61B 5/0066; A61B 34/20; A61B 6/12; A61B 2034/2051; A61B 2034/107; A61B 2090/376; G06T 7/0012; G06T 2207/10101; G06T 2207/30041; G06T 7/62; G06T 19/006; G06T 7/33; G06T 19/20; G06T 2207/10072;

(Continued)

(56) References Cited

U.S. PATENT DOCUMENTS

| 6,114,320 A | 9/2000 | Aiello et al. |
| 7,768,652 B2 * | 8/2010 | Everett ............... A61B 5/0059 356/497 |

(Continued)

FOREIGN PATENT DOCUMENTS

| JP | 2012-020061 | 2/2012 |
| WO | 2010/140476 | 12/2010 |

OTHER PUBLICATIONS

Chen et al., Model-based measurement of food portion size for image-based dietary assessment using 3D/2D registration, Aug. 30, 2013 [retrieved Jun. 30, 2018], Measure Science and Technology, vol. 24, No. 10, pp. 1-11. Retrieved from the Internet: http://iopscience.iop.org/article/10.1088/0957-0233/24/10/105701/meta.*

(Continued)

*Primary Examiner* — Andrew M Moyer
*Assistant Examiner* — Dennis Rosario
(74) *Attorney, Agent, or Firm* — Casimir Jones S.C.; J. Mitchell Jones

(57) ABSTRACT

Provided herein is technology relating to analysis of images and particularly, but not exclusively, to methods and systems for determining the area and/or volume of a region of interest using optical coherence tomography data. Some embodiments provide for determining the area and/or volume of a lesion in retinal tissue using three-dimensional optical coherence tomography data and a two-dimensional optical coherence tomography fundus image.

32 Claims, 9 Drawing Sheets

(58) Field of Classification Search
CPC ...... G06T 2207/10081; G01B 9/02091; G02B 27/0172; G02B 2027/0178; G06F 3/013
See application file for complete search history.

(56) References Cited

U.S. PATENT DOCUMENTS

| | | | |
|---|---|---|---|
| 7,939,021 B2 | 5/2011 | Smith et al. | |
| 8,684,528 B2* | 4/2014 | Fujimura | A61B 3/102 351/206 |
| 8,913,793 B2 | 12/2014 | Everett et al. | |
| 8,944,597 B2 | 2/2015 | Meyer | |
| 9,149,183 B2* | 10/2015 | Iwase | A61B 3/102 |
| 9,375,195 B2* | 6/2016 | Kamen | A61B 8/0841 |
| 9,700,210 B2* | 7/2017 | Iwase | A61B 5/0066 |
| 2003/0199769 A1 | 10/2003 | Podoleanu | |
| 2006/0228011 A1 | 10/2006 | Everett | |
| 2008/0187095 A1 | 8/2008 | Boone et al. | |
| 2012/0165354 A1 | 6/2012 | McLaughlin et al. | |
| 2013/0181976 A1 | 7/2013 | Dastmalchi et al. | |
| 2014/0152957 A1 | 6/2014 | Reisman et al. | |

OTHER PUBLICATIONS

Domalpally (2013) "Circularity Index as a Risk Factor for the Progression of Geographic Atrophy" Ophthalmology 120(12): 2666-71.

Hu et al. (2013) "Segmentation of Geographic Atrophy in Spectral-Domain Optical Coherence Tomography and Fundus Autofluorescence Images" Invest Ophth Vis Sci 54: 8375-83.

Ishikawa et al. (2005) "Macular Segmentation with Optical Coherence Tomography" Invest Ophthalmol Vis Sci 46: 2012.

Jiao et al (2005) "Simultaneous acquisition of sectional and fundus ophthalmic images with spectral-domain optical coherence tomography" Optics Express 13: 444-452.

Jorgensen et al (2007) "Enhancing the signal-to-noise ratio in ophthalmic optical coherence tomography by image registration? method and clinical examples" J Biomed Opt 12: 041208.

Paunescu et al. "Reproducibility of nerve fiber thickness, macular thickness, and optic nerve head measurements using StratusOCT" Invest Ophthalmol Vis Sci 45(6): 1716-24.

Pieroni et al. (2006) "Ultrahigh resolution optical coherence tomography in non-exclusive age related macular degeneration" Br J Ophthalmol 90(2): 191-7.

Wojtkowski et al. (2002) "In vivo human retinal imaging by Fourier domain optical coherence tomography" J Biomed Opt 7: 457-63.

Wojtkowski et al. (2003) "Real-time in vivo imaging by high-speed spectral optical coherence tomography" Opt Lett 28: 1745-47.

Wojtkowski et al. (2004) "Ophthalmic imaging by spectral optical coherence tomography" Am J Ophthalmol 138: 412-9.

Wojtkowski et al. (2005) "Three-dimensional retinal imaging with high-speed ultrahigh-resolution optical coherence tomography" Ophthalmology 112: 1734-46.

Yehoshua et al. (2014) "Comparison of Geographic Atrophy Measurements from the OCT Fundus Image and the Sub-RPE Slab Image" Ophthalmic Surg Lasers Imaging Retina 44: 127-32.

Supplementary EP Search Report, EP Patent Application No. 16769351.4, dated Nov. 20, 2018, 4 pages.

\* cited by examiner

1

2

3

4

IMAGE ANALYSIS

CROSS REFERENCE TO RELATED APPLICATIONS

This application claims the benefit U.S. Provisional Patent Application No. 62/269,601 filed Dec. 18, 2015 and U.S. Provisional Patent Application No. 62/138,485, filed Mar. 26, 2015, each of which is incorporated by reference in its entirety.

FIELD

Provided herein is technology relating to analysis of images and particularly, but not exclusively, to methods and systems for determining the area and/or the volume of a region of interest using optical coherence tomography data.

BACKGROUND

Clinicians and researchers increasingly use image data representing biological tissues, e.g., to identify and diagnose tissue anomalies and pathologies. Imaging using optical coherence tomography (OCT) is an imaging method that produces cross-sectional images of tissue morphology (see, e.g., Pieroni et al. (2006) "Ultrahigh resolution optical coherence tomography in non-exclusive age related macular degeneration" Br J Ophthalmol 90(2): 191-7).

In particular, OCT provides excellent visualization of retinal tissue abnormalities using cross-sectional pseudo-color or grayscale images of the tissue reflectivity. However, quantifying the size (e.g., determining the lateral extent, area, and/or volume) of localized retinal tissue abnormalities is not trivial. For example, determining the en face area of a retinal abnormality in OCT data alone (e.g., without reference to a fundus image) involves a user identifying the border of the retinal abnormality in each of many OCT cross-sectional images. This is a very laborious process and is not accurate when the abnormality has multiple loci, a complex or irregular shape, or when the extent of the abnormalities increases laterally. Further, OCT segmentation is typically based on known anatomical tissue layers (e.g., in a normal subject) and thus is not necessarily based on the border of the abnormality.

For example, extant technologies for evaluating a volumetric size (e.g., the volume of the retinal cystoid space) often include steps wherein a clinician views an OCT image and manually segments various anatomical layers (e.g., the inner limiting membrane (ILM) and the retinal pigment epithelium (RPE)) shown in the image. Then, software performs a volumetric calculation, e.g., by a trapezoidal integration of multiple frames of the thickness between the anatomical layers. Using such a technique, while the resultant value includes the volume of the abnormality under examination (e.g., the cystoid space), it also includes the volume of the neighboring (e.g., healthy) tissue that may not be relevant to the calculation related to the abnormality. Further, some extant technologies are associated with measuring the variance of the volume of a tissue from the development of the abnormality by comparison to a normative database. These measurements, however, are confined to the fixed regions and the fixed segmented layers that have to be measured to generate the normative data. In addition, these technologies are limited in that such measurements are not typically made and thus appropriate data are not available.

In addition, quantitative analysis of OCT data has been used in the diagnosis and treatment of macular degeneration (e.g., wet and dry age-related macular degeneration (AMD)). For example, retinal thickness measurements have been used for some patients to monitor the effectiveness of treatment with anti-vascular endothelial growth factor (VEGF) agents (e.g., Ranibizumab marketed as, e.g., "Lucentis"; aflibercept marketed as, e.g., "Eylea"). Measurement of retinal thickness (e.g., measurement of a fixed 1-mm (e.g., 0.1 to 10 mm) diameter region centered on the macula) is used to estimate the subretinal and/or the intraretinal fluid accumulation and is generally accepted by the FDA as an imaging endpoint. In addition, new combination therapies are available that target both VEGF and platelet-derived growth factor (PDGF). While the anti-PDGF treatment is administered to reduce the size of the central neovascularization (CNV) complex associated with macular degeneration, quantitative analysis of this treatment in human clinical trials is presently limited. Several preliminary studies have attempted to quantify the lateral extent (e.g., the area) of the CNV lesion complex using fluorescein angiography images but have not quantified the area or volume of a CNV lesion based on OCT data (see, e.g., Jaffe et al. (2015) "A phase 1 study of intravitreous E10030 in combination with Ranibizumab in neovascular AMD" Ophthalmology (Manuscript no. 2015-470, in press); Boyer (2009) "Combination inhibition of PDGF and VEGF for treatment of neovsacular AMD", ARVO abstract).

Area measurements of retina lesions also find use as anatomic endpoints, e.g., for monitoring and treating geographic atrophy (GA) of the retina pigment epithelium (RPE) in AMD. In particular, an increase in the area of the GA region over time is considered a measure of disease progression. In addition, a clinically important measure is the proximity of the boundary of the GA (as measured by loss of the RPE and/or disappearance of the external limiting membrane layer of the retina) to the retinal area for the center of vision, the fovea. A treatment that slows the progression of GA (e.g., slows the increase of the area of the GA region as a function of time) and/or delays the invasion of the GA region toward and/or into the fovea may preserve vision and/or minimize the loss of vision. Numerous treatments for GA are under clinical investigation at this time and would benefit from technologies that measure and/or monitor the size and/or change in size of a GA region. Current technologies for tracking GA progression in both clinical care and clinical research are based on measuring the area of a GA region using en face imaging modalities such as, e.g., retina photographs, fundus autofluorescence, fluorescein angiograms, etc. Further, present OCT-based measurements of GA are based on voxel projection images (see, e.g., Hu (2013) "Segmentation of Geographic Atrophy in Spectral-Domain Optical Coherence Tomography and Fundus Autofluorescence Images" Invest Ophth Vis Sci 54: 8375-83; Yehoshua (2014) "Comparison of Geographic Atrophy Measurements from the OCT Fundus Image and the Sub-RPE Slab Image" Ophthalmic Surg Lasers Imaging Retina 44: 127-32).

Thus, although OCT data are valuable to clinicians and researchers, the utility of OCT technologies would benefit from improved image analysis for measuring the sizes of tissue anomalies and pathologies, e.g., by directly correlating eye microstructures using three-dimensional (e.g., volumetric) metrics and two-dimensional (e.g., en face) display of data.

SUMMARY

The metric assessment (e.g., determination of one or more sizes (e.g., distances, areas, volumes, etc.)) and tracking of localized tissue abnormalities provides a diagnostic tool, e.g., for the treatment of subjects. In particular, the technology described herein relates to a method of pairing optical coherence tomography (OCT) three-dimensional (e.g., volume and/or cross-sectional) data with a two-dimensional image (e.g., a fundus image, a color photograph, infrared reflectance image, angiographic frame, integration of three-dimensional data, etc.) and using the two-dimensional image and/or cross sectional data (e.g., two-dimensional "slices" of three-dimensional data) as the primary source to determine the extent (e.g., in linear (e.g., one-dimensional), two-dimensional, and/or three-dimensional space) of a tissue abnormality.

In various embodiments, the fundus image is or is not acquired together with the OCT data during data acquisition. In some embodiments, the fundus image is registered with the OCT data (e.g., OCT image) post hoc. In some embodiments, the OCT data (e.g., OCT image) is registered pixel-by-pixel with the fundus image. In some embodiments, the reference fundus image is an en face pixel display of OCT data.

In some embodiments, a user indicates a boundary of the region of interest (e.g., abnormality, lesion, CNV complex, etc.) on a display showing the fundus image and/or by examination of the OCT data, thus providing a digital representation (e.g., a pixel representation) of the border of the region of interest (e.g., abnormality, lesion, CNV complex, etc.). The digital representation of the region of interest (e.g., abnormality, lesion, CNV complex, etc.) is mapped to a digital representation (e.g., a pixel representation) of the OCT three-dimensional data and the software determines the area and/or volume of the region of interest (e.g., abnormality, lesion, CNV complex, etc.) from the fundus image and/or OCT data according to the technology provided herein.

Accordingly, the technology provided herein relates in some embodiments to a method for determining the distance, length, or location; area; and/or volume of a region of interest of a biological tissue using optical coherence tomography (OCT). In some embodiments, the method comprises acquiring three-dimensional OCT data comprising at least a first segment (e.g., an anterior segment) and a second segment (e.g., a posterior segment) defining the region of interest; acquiring two-dimensional image data (e.g., OCT fundus data, a photograph, etc.) comprising the region of interest; providing a boundary around the region of interest in the two-dimensional image data, the boundary enclosing an area A; calculating the volume v within the boundary of area A and between the first segment and the second segment; calculating the average thickness t between the first segment and the second segment along the boundary (e.g., along the perimeter of area A); and calculating the volume V of the region of interest:

$$V=v-(t\times A)$$

The technology is not limited by the shape of the boundary. For example, in some embodiments the boundary is a circle, ellipse, polygon (e.g., triangle, quadrilateral (e.g., square, rectangle, trapezoid, parallelogram, rhombus, etc.), etc.), or other shape, and in some embodiments the boundary is an irregular shape. In some embodiments, the boundary is any shape whose perimeter surrounds the region of interest (e.g., in a fundus image or other two-dimensional representation (e.g., projection, integration, slice, cross-section, etc.) of three-dimensional data) and that has an area (e.g., an area that is the same size or larger than the limits of the lesion and/or region of interest). Some embodiments comprise determining a greatest linear distance across the region of interest in the two-dimensional OCT fundus data. In some embodiments, the greatest linear distance is determined or provided by a computer and in some embodiments the greatest linear distance is determined or provided by a user. In some embodiments, a linear measurement provides a distance of a lesion boundary to an anatomic location in the retina (e.g., a distance to the fovea from the nearest edge of a lesion).

Particular embodiments relate to OCT data wherein the three-dimensional OCT data is a three-dimensional OCT image and wherein the two-dimensional OCT fundus data is a two-dimensional image, e.g., produced by integrating three-dimensional OCT data, or wherein the two-dimensional OCT fundus data is a photograph (e.g., a digital image).

In some preferred embodiments, a user draws the boundary around the region of interest (e.g., by interacting with a computer to provide a pixel representation of the boundary superimposed on the fundus image); in specific embodiments, a user draws the boundary around the region of interest using a computer input device (e.g., a cursor control device, e.g., a mouse, light pen, stylus, touch screen, trackball, trackpad, joystick, etc.). In some embodiments, automated image processing draws the boundary around the region of interest. For example, in some embodiments a user identifies points on an image defining the edge of a region of interest and an automated method (e.g., a software method) connects the points to provide a continuous boundary encompassing the region of interest. The automated image analysis algorithm analyses the imaging data and the location of the user-defined points to provide a boundary encompassing the region of interest (e.g., by using an interpolation algorithm to define points between the user-defined points and connecting all points with a line encompassing the region of interest).

Embodiments of the technology are provided to provide an area and/or a volume of a region of interest (e.g., tissue abnormality, lesion, CNV complex, etc.). Embodiments of the technology calculate the area and/or volume of the region of interest (e.g., abnormality, lesion, CNV complex, etc.) by identifying a region of the tissue that is normal. Accordingly, some embodiments comprise providing the boundary on normal biological tissue such that the region of interest is circumscribed by an unaffected boundary region or through the use of a normative database (e.g., the perimeter of the boundary is provided on a region of the image data corresponding to normal tissue). Some embodiments provide for outputting the area and/or volume of the region of interest to a user (e.g., on a display, over a network, printed on paper, etc.).

In some embodiments, the region of interest is a lesion in the biological tissue. In particular embodiments, the biological tissue is retinal tissue and the region of interest is a retinal lesion. For example in some embodiments the region of interest is a central neovascularization (CNV) lesion complex, e.g., associated with macular degeneration (e.g., wet macular degeneration, dry macular degeneration). In other embodiments, the region of interest is a defect of the retina pigment epithelium layer and/or the volume of a specific retina layer overlying a region of interest (e.g., the outer nuclear layer of the retina over an area of RPE loss).

Additional methods relate to treating a subject having a tissue abnormality (e.g., abnormal tissue growth, CNV lesion, etc.). Thus, some embodiments provide a method of treating a subject having a tissue abnormality, the method comprising acquiring an area and/or a volume of the tissue abnormality according to a method provided herein and administering a treatment to the subject based on the area and/or the volume of the tissue abnormality. Additional embodiments relate to a method of identifying that a treatment of a subject having a tissue abnormality is successful, the method comprising calculating a first area and/or a first volume of the tissue abnormality according to a method as described herein; administering a treatment to the subject; calculating a second area and/or a second volume of the tissue abnormality according to a method described herein; and identifying the treatment of the patient as effective when the second area and/or the second volume of the tissue abnormality is less than the first area and/or the first volume of the tissue abnormality. For example, in some embodiments an effective treatment reduces the area and/or the volume of the tissue abnormality by 1% to 100% (e.g., from 5, 10, 15, 20, 25, 30, 35, 40, 45, 50, 55, 60, 65, 70, 75, 80, 85, 90, or 95 to 100%).

Some embodiments relate to treating a subject and monitoring the progress in treatment using a linear measurement, e.g., a measurement that provides a distance of a lesion boundary to an anatomic location in the retina (e.g., a distance to the fovea from the nearest edge of a lesion). For example, in some embodiments an effective treatment increases the distance between the lesion and the anatomical feature (e.g., the fovea) by 1% to 100% (e.g., from 5, 10, 15, 20, 25, 30, 35, 40, 45, 50, 55, 60, 65, 70, 75, 80, 85, 90, or 95 to 100%).

Accordingly, in some embodiments a first area and/or a first volume of the tissue abnormality is measured according to a method provided herein; a second area and/or a second volume of the tissue abnormality is measured according to a method provided herein after the first area and/or the first volume measurement; and a second area and/or a second volume that is less than the first area and/or first volume indicates that the treatment is effective. In some embodiments a first distance of the tissue abnormality from an anatomical feature is measured according to a method provided herein; a second distance of the tissue abnormality from the anatomical feature is measured according to a method provided herein after the first distance measurement; and a second distance that is greater than the first distance indicates that the treatment is effective Thus, in some embodiments in which the treatment is indicated as effective, the treatment is modified (e.g., dose decreased), discontinued, changed, etc. In some embodiments, the distance, area, and/or volume measurements indicate that one treatment should replace another treatment. In some embodiments, the distance, area, and/or volume measurements indicate that two or more treatments should be combined.

In some embodiments, the areas and/or volumes indicate that the treatment is effective and that it should thus be maintained without modification. Conversely, an increase in the second area and/or the second volume measurement relative to the first area and/or first volume may indicate disease progression. In some embodiments, tissue loss (e.g., atrophy) is determined by an increasing negative value of the second measurement (e.g., the difference between the first area and/or first volume and subsequent second areas and/or second volumes increases). In some embodiments, a reference region is selected in a plurality of images to provide a common reference point for comparing and/or aligning (e.g., registering) the plurality of images. For example, in some embodiments, images from different time points are registered with each other (e.g., using anatomical (e.g., tissue) landmarks such as retinal blood vessels, the optic nerve head, etc.).

In some embodiments, a subject is tested to assess the presence, the absence, or the level of a tissue abnormality, e.g., by acquiring an area and/or a volume of the tissue abnormality according to a method provided herein, and thereafter the subject is treated based on the outcome of the test. In some embodiments, a subject is tested, treated, and then tested again to monitor the response to therapy. In some embodiments, cycles of testing and treatment may occur without limitation to the pattern of testing and treating (e.g., test/treat, test/treat/test, test/treat/test/treat, test/treat/test/treat/test, treat/test/treat, test/treat/treat/test/treat/treat, etc), the periodicity, or the duration of the interval between each testing and treatment phase.

The technology provided herein provides several advantages relative to existing OCT metric analysis. For example, existing analysis software for processing OCT data scans uses a sampled area that is fixed (e.g., a gridded circle having a 6-mm diameter and centered on the fovea) and segments the inner and outer limits of the tissue layers within that circle. The area of the total tissue and the volume of the total tissue area are calculated by integrating all points within the fixed reference circle. However, the actual area and/or volume of the localized lesion (e.g., tissue and swelling from a choroidal neovascular membrane) may be only a small fraction of the total sampled area and, consequently, a very large area of healthy tissue may be included in the measured area and/or volume of the grid using the existing technology. Thus, a small relative change in the 6-mm circle volume (e.g., 5%) may represent a very large relative change in the volume of the localized lesion (e.g., a decrease of 80%). In contrast, the technology described herein provides a more accurate and sensitive biomarker for measuring the relative metric (e.g., area or volume) change of localized lesions in data for analysis.

Additional embodiments provide a system for determining the area and/or volume of a region of interest of a biological tissue, the system comprising an OCT apparatus and software to calculate an area and/or volume of the region of interest according to the methods described herein. Further embodiments comprise a component configured to display three-dimensional OCT data and two-dimensional fundus data to a user. Yet additional embodiments of systems comprise a component configured to accept input from a user to provide the boundary around the region of interest in the two-dimensional OCT fundus data. Particular embodiments provide a component to output the area and/or volume of the region of interest, e.g., to a user.

Some embodiments provide a method for determining the area and/or volume of a retinal lesion, the method comprising acquiring SD-OCT data (e.g., three-dimensional SD-OCT data); displaying a fundus image of the SD-OCT data on a display (e.g., produced from the three-dimensional SD-OCT data; acquired simultaneously with the three-dimensional SD-OCT data; and/or acquired at a different time than the three-dimensional SD-OCT data); and providing a boundary around a region of interest by acquiring user input from a user who interacts with the displayed two-dimensional fundus image using an input device, the boundary enclosing an area A.

In particular embodiments provided herein is a method for determining the area and/or volume of a retinal lesion, the method comprising providing a three-dimensional SD-OCT image comprising a first retinal segment and a second retinal segment comprising a retinal lesion; providing a two-dimensional SD-OCT fundus image comprising the retinal lesion; determining a greatest linear distance across the retinal lesion in the two-dimensional fundus image; circumscribing a circle around the retinal lesion in the two-dimensional fundus image, the circle having a diameter d greater than or equal to the greatest linear distance across the retinal lesion in the two-dimensional fundus image; calculating the average thickness t between the first retinal segment and the second retinal segment along the perimeter of the circle; calculating the volume v within the circle and between the first segment and second segment; and calculating the volume V of the retinal lesion:

$$V=v-(t\times\Pi\times(d/2)^2)$$

In particular embodiments provided herein is a method for determining the area and/or volume of central neovascularization (CNV) lesion, e.g., associated with macular degeneration, the method comprising providing a three-dimensional SD-OCT image comprising a first retinal segment and a second retinal segment comprising a CNV lesion; providing a two-dimensional SD-OCT fundus image comprising the CNV lesion; determining a greatest linear distance across the CNV lesion in the two-dimensional fundus image; circumscribing a circle around the CNV lesion in the two-dimensional fundus image, the circle having a diameter d greater than or equal to the greatest linear distance across the CNV lesion in the two-dimensional fundus image; calculating the average thickness t between the first retinal segment and the second retinal segment along the perimeter of the circle; calculating the volume v within the circle and between the first segment and second segment; and calculating the volume V of the CNV lesion;

$$V=v-(t\times\Pi\times(d/2)^2)$$

Some further embodiments provide a method for determining the area and/or volume of a CNV lesion, the method comprising acquiring SD-OCT data (e.g., three-dimensional SD-OCT data); displaying a fundus image of the SD-OCT data on a display (e.g., produced from the three-dimensional SD-OCT data; acquired simultaneously with the three-dimensional SD-OCT data; and/or acquired at a different time than the three-dimensional SD-OCT data); and providing a boundary around a region of interest by acquiring user input from a user who interacts with the displayed two-dimensional fundus image using an input device, the boundary enclosing an area A.

In some embodiments, the method further comprises segmenting the SD-OCT data, e.g., to provide at least a first segment and a second segment. In some embodiments, the segments correspond to anatomical features (e.g., tissues, tissue layers, etc.) and in some embodiments the segments do not necessarily correspond to histological, biological, and/or anatomical features (e.g., the segments are appropriate for analysis of the region of interest as provided by the technology herein and not necessarily with respect to histological, biological, and/or anatomical features).

In yet additional embodiments, the method comprises calculating the volume v within the boundary and between the first segment and the second segment; calculating the average thickness t between the first segment and the second segment along the boundary; and/or calculating the volume of the region of interest $V=v-(t\times A)$.

In some embodiments, the method comprises identifying regions and/or boundaries of RPE loss from OCT B scans in eyes with geographic atrophy of the retina pigment epithelium. In some embodiments, identifying the regions and/or boundaries of RPE loss comprises registering the locations of the regions and/or boundaries in the OCT scans with the corresponding locations in the en face fundus image. In some embodiments, the area A is then calculated using segmentation (e.g., manual segmentation by the user and/or automated segmentation) of the boundary annotated to the en face image. Accordingly, embodiments provide that images acquired at multiple time points are assessed according to the same methods and differences in lesion boundaries and/or lesion areas in a plurality of images are used to assess changes in boundaries, areas, shapes, etc., e.g., to provide an assessment of disease progression, treatment, etc.

In some particular embodiments, the input device is a touchscreen—that is, the user interacts with the data displayed as an image on a touchscreen and the user provides commands and indicates the boundary of the region of interest by providing input using the touchscreen (e.g., by drawing with a finger, stylus, etc. on the touchscreen and/or using another input device). In some embodiments, the methods further comprise displaying the boundary on the display (e.g., superimposed on the SD-OCT image). For example, in some embodiments, a distance (e.g., a distance d, a distance from a lesion (e.g., a lesion boundary) to an anatomical feature, etc.) is displayed on the display, an area A of the volume of interest is displayed on the display, a volume of the region of interest V is displayed on the display, and/or the average thickness t is displayed on the display. In some embodiments, as the boundary is changed by user interaction, the methods comprise updating the volume of the region of interest V on the display and updating the average thickness t on the display as the boundary changes.

Additional embodiments will be apparent to persons skilled in the relevant art based on the teachings contained herein.

BRIEF DESCRIPTION OF THE DRAWINGS

These and other features, aspects, and advantages of the present technology will become better understood with regard to the following drawings:

FIG. 2D-2 and FIG. 2D-4 show a volume n defined by the boundary extended through the sample over distance t. The volume n is the product of A and t.

Figure 1:
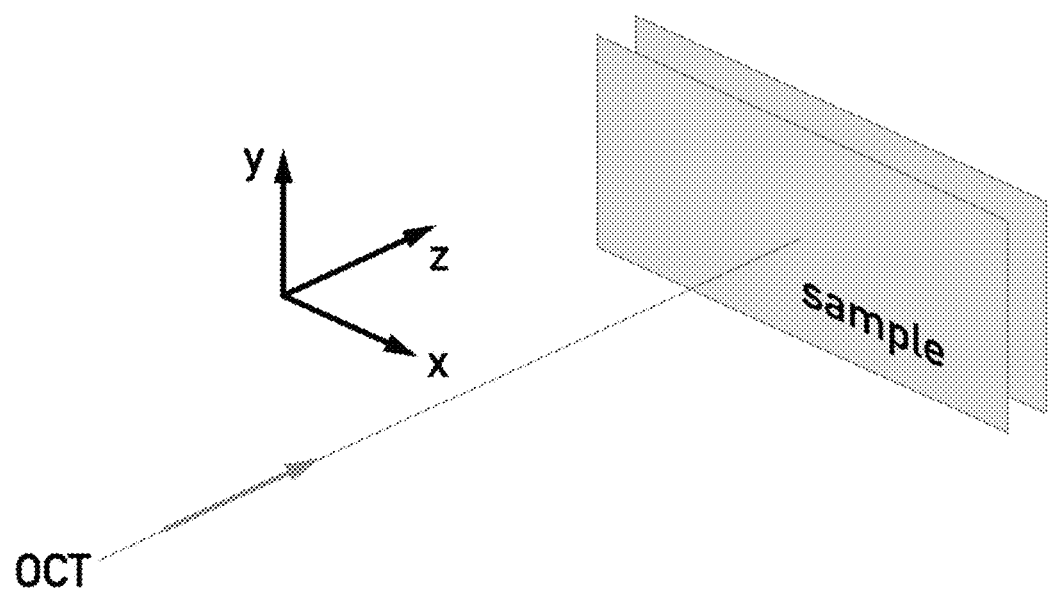
FIG. 1 is a schematic drawing showing an exemplary coordinate system in relation to an OCT apparatus ("OCT") and a sample ("sample") imaged by the OCT apparatus.

It is to be understood that the figures are not necessarily drawn to scale, nor are the objects in the figures necessarily drawn to scale in relationship to one another. The figures are depictions that are intended to bring clarity and understanding to various embodiments of apparatuses, systems, and methods disclosed herein. Wherever possible, the same reference numbers will be used throughout the drawings to refer to the same or like parts. Moreover, it should be appreciated that the drawings are not intended to limit the scope of the present teachings in any way.

DETAILED DESCRIPTION

Provided herein is technology relating to analysis of images and particularly, but not exclusively, to methods and systems for determining the volume of a region of interest using optical coherence tomography data.

In this detailed description of the various embodiments, for purposes of explanation, numerous specific details are set forth to provide a thorough understanding of the embodiments disclosed. One skilled in the art will appreciate, however, that these various embodiments may be practiced with or without these specific details. In other instances, structures and devices are shown in block diagram form. Furthermore, one skilled in the art can readily appreciate that the specific sequences in which methods are presented and performed are illustrative and it is contemplated that the sequences can be varied and still remain within the spirit and scope of the various embodiments disclosed herein. The section headings used herein are for organizational purposes only and are not to be construed as limiting the described subject matter in any way.

All literature and similar materials cited in this application, including but not limited to, patents, patent applications, articles, books, treatises, and internet web pages are expressly incorporated by reference in their entirety for any purpose. Unless defined otherwise, all technical and scientific terms used herein have the same meaning as is commonly understood by one of ordinary skill in the art to which the various embodiments described herein belongs. When definitions of terms in incorporated references appear to differ from the definitions provided in the present teachings, the definition provided in the present teachings shall control.

Definitions

To facilitate an understanding of the present technology, a number of terms and phrases are defined below. Additional definitions are set forth throughout the detailed description.

Throughout the specification and claims, the following terms take the meanings explicitly associated herein, unless the context clearly dictates otherwise. The phrase "in one embodiment" as used herein does not necessarily refer to the same embodiment, though it may. Furthermore, the phrase "in another embodiment" as used herein does not necessarily refer to a different embodiment, although it may. Thus, as described below, various embodiments of the invention may be readily combined, without departing from the scope or spirit of the invention.

In addition, as used herein, the term "or" is an inclusive "or" operator and is equivalent to the term "and/or" unless the context clearly dictates otherwise. The term "based on" is not exclusive and allows for being based on additional factors not described, unless the context clearly dictates otherwise. In addition, throughout the specification, the meaning of "a", "an", and "the" include plural references. The meaning of "in" includes "in" and "on."

As used herein, "optical coherence tomography" or "OCT" refers to a medical imaging technique that uses light to capture micrometer-resolution, three-dimensional images from within optical scattering media (e.g., biological tissue). Optical coherence tomography is based on low-coherence interferometry, typically employing near-infrared light. The use of relatively long wavelength light allows it to penetrate into the scattering medium.

As used herein, an axis extending from an OCT apparatus and the sample (e.g., tissue) under examination is the z-axis. Planes normal to the z-axis are x-y planes. See, e.g., FIG. 1.

As used herein, an "A-scan" is an amplitude modulation scan that provides one-dimensional information in the direction of the z-axis, e.g., an axial depth scan. For example, in some embodiments an A-scan is used to determine the length of a tissue, tissue segment, tissue feature, etc. in the direction of (or substantially, essentially, or approximately along) the z-axis or to determine the location of a tissue segment or tissue feature along a path in the direction of the z-axis. See, e.g., FIG. 1.

As used herein, a "B-scan" is a two-dimensional, cross-sectional or "profile" view of the sample under examination, e.g., a two-dimensional scan in the x-z or y-z planes. The two-dimensional cross-sectional B-scan may be produced by laterally combining a series of axial depth A-scans. See, e.g., FIG. 1.

As used herein, a "C-scan" is a two-dimensional, cross-sectional or "plan" view of the sample under examination, e.g., a two-dimensional scan in the x-y plane. See, e.g., FIG. 1.

As used herein, the term "image segmentation" or "segmentation" refers to a digital method of dividing image data into regions that may consist of a pixel area that is homogeneous in terms of certain characteristics, or of an area that groups pixels corresponding to an object that is visualized in the image. In this way, multiple layers or image fragments may be created, for example, to represent tissue layers or regions of a tissue that have similar characteristics. Accordingly, segmentation refers to the process of partitioning a digital image into multiple regions (e.g., sets of pixels). In some embodiments, the goal of segmentation is to simplify and change the representation of an image into something that is more meaningful and easier to analyze. Image segmentation is typically used to locate objects and boundaries (lines, curves, etc.) in images. The result of image segmentation is a set of regions that collectively cover the entire image, or a set of contours extracted from the image. In some embodiments, the segments correspond to biological features (e.g., tissues, tissue layers, etc.). However, the technology is not limited to segments that correspond to biological features and, in various embodiments, the segments correspond to any division of the image appropriate for the methods, technology, analysis, etc. desired by the user. Methods for finding and segmenting a desired tissue layer or boundary surface are well-known in the art. See, e.g., Ishikawa et al. (2005) "Macular Segmentation with Optical Coherence Tomography" *Invest Ophthalmol Vis Sci* 46; 2012, incorporated herein by reference in its entirety.

A "system" denotes a set of components, real or abstract, comprising a whole where each component interacts with or is related to at least one other component within the whole.

As used herein, a "region of interest" refers to a region (e.g., portion, sub-sample, sub-volume, etc.) of an image and/or of a sample (e.g., a tissue) that is assessed by the methods provided herein. In particular embodiments, the "region of interest" refers to a tissue abnormality, lesion, or other feature of a tissue that is subjected to the metric analysis (e.g., measurement of an area; measurement of a volume) provided herein.

As used herein, an "increase" or a "decrease" refers to a detectable (e.g., measured) positive or negative change in the value of a variable (e.g., a volume) relative to a previously measured value of the variable, relative to a pre-established value, and/or relative to a value of a standard control. An increase is a positive change relative to the previously measured value of the variable, the pre-established value, and/or the value of a standard control. Similarly, a decrease is a negative change relative to the previously measured value of the variable, the pre-established value, and/or the value of a standard control. Other terms indicating quantitative changes or differences, such as "more" or "less," are used herein in the same fashion as described above.

Description

Optical coherence tomography (OCT) is a method of using interferometry to determine the echo time delay and magnitude of backscattered light reflected off an object of interest. OCT is similar in principle to ultrasound, but in OCT light is used instead of sound and interferometry is used to determine the time delay of reflected light. The original OCT method, known as TD-OCT, encoded the location of each reflection in the time information relating the position of a moving reference mirror to the location of the reflection.

An advance in OCT was the use of light wavelengths instead of time delay to determine the spatial location of reflected light. Fourier transform analysis is used to provide a technology based in the spectral domain (SD-OCT) rather than in the time domain (TD-OCT). SD-OCT acquires all information in a single axial scan through the tissue simultaneously by evaluating the frequency spectrum of the interference between the reflected light and a stationary reference mirror. See, e.g., Wojtkowski et al. (2004) "Ophthalmic imaging by spectral optical coherence tomography" *Am J Ophthalmol* 138: 412-9; Wojtkowski et al. (2002) "In vivo human retinal imaging by Fourier domain optical coherence tomography" *J Biomed Opt* 7: 457-63; and Wojtkowski et al. (2003) "Real-time in vivo imaging by high-speed spectral optical coherence tomography" *Opt Lett* 28: 1745-47, each incorporated herein in its entirety by reference.

SD-OCT is advantageous over TD-OCT because the interference pattern is split by a grating into its frequency components and all of these components are simultaneously detected by a charge-coupled device (CCD), thus making it faster. Further, data are acquired without mechanical movement of a scanning mirror as in TD-OCT. The SD-OCT technique significantly increases signal-to-noise ratio and increases the speed of data collection by a factor of 50 relative to TD-OCT. For example, a conventional time-domain OCT functions at 400 A-scan/s, while an SD-OCT system scans at 20,000 A-scan/s. Because of the increase in speed, a single cross-sectional scan of 1000 A-scans can be captured, processed, streamed to disk, and displayed in 60 ms (or $\frac{1}{42}$ of the time required for a time-domain scan). Because of this speed, there is less movement of the subject during the SD-OCT scan and thus a more stable image is produced with a significant decrease in artifact of the image. Also because of this speed, a stack of 100 cross-sectional scans can be acquired in the time normally used to gather 6 low-resolution cross-sectional scans on a time-domain system. The image stack can be processed to produce a three dimensional representation of structures (see Wojtkowski et al. (2005) "Three-dimensional retinal imaging with high-speed ultrahigh-resolution optical coherence tomography" *Ophthalmology* 112: 1734-46, incorporated herein by reference).

SD-OCT imaging thus frequently uses a series of scans. Focusing the light beam to a point on the surface of the sample under test, and recombining the reflected light with the reference will yield an interferogram with sample information corresponding to a single A-scan (along the z-axis). Scanning of the sample can be accomplished by either scanning the light on the sample, or by moving the sample under test. A linear scan will yield a two-dimensional data set corresponding to a cross-sectional image (e.g., in the x-z plane), whereas an area scan achieves a three-dimensional data set corresponding to a volumetric image (e.g., a volume in the x-y-z space), also called full-field OCT. Accordingly, a stack of B-scans can undergo further analysis and produce a three dimensional representation of structures.

Furthermore, it is possible to collapse three-dimensional OCT volumes (e.g., along a z-axis (e.g., along the depth axis)) to a two-dimensional representative image along any plane of a 3D volume using algorithms to calculate a single representative pixel intensity for each line in the projection. One technique of obtaining such an "en face" picture with optical coherence tomograms is referred to as a summed voxel projection (SVP) (see, e.g., Jiao et al (2005) "Simultaneous acquisition of sectional and fundus ophthalmic images with spectral-domain optical coherence tomography" Optics Express 13: 444-452, incorporated herein by reference).

Image registration and alignment is based on tissue structural features, e.g., to correct motion artifacts (see, e.g., Jorgensen et al (2007) "Enhancing the signal-to-noise ratio in ophthalmic optical coherence tomography by image registration-method and clinical examples" J Biomed Opt 12: 041208). For example, 3D data sets are presented with all pixels in each given axial scan summed to produce an OCT fundus image, which resembles a 2D photograph summing reflections from all tissue layers. The OCT fundus image can be used for image alignment or registration based on tissue features, such as blood vessel continuities or discontinuities. The 3D OCT can also be aligned or registered to a fundus photograph acquired simultaneously or nearly so. Automated or manual segmenting defines tissue layers in the SD-OCT data.

Because of the unique optically clear pathway through the eye, OCT has been used for imaging disorders affecting the retina. In some current uses, obtaining and processing each of a series of 500×500-pixel images takes on the order of seconds and the technology can now acquire 3D data sets comprising several hundred scans of 200×200×1024 pixels in 2 seconds. In exemplary embodiments, this method is used to scan through the layers of a structured tissue sample such as the retina with very high axial resolution (3 to 15 μm), providing images demonstrating 3D structure.

SD-OCT images show multiple tissue (e.g., retinal) layers of different reflectivity. These tissue layers are typically segmented using a computer algorithm and/or by manual tracing. When an abnormality occurs in a tissue (e.g., in the retina (e.g., a "retinal lesion")), the layered structure of the tissue (e.g., retina) is altered, resulting in a thickening, thinning, or loss of tissue (e.g., retinal, RPE) layers at the corresponding location, which are imaged by SD-OCT. In some embodiments, the lesion is present in the image as a protrusion in one of the segmented features of the image. Thus, volumetric analysis of tissue abnormalities, lesions, etc. is desirable to evaluate, monitor, and treat the abnormalities, lesions, etc.

Examples of OCT display image technologies are provided, e.g., by U.S. Pat. No. 8,944,597, incorporated herein by reference. See also U.S. Pat. No. 8,913,793 (incorporated herein by reference in its entirety), which relates to display of OCT images in various ways, including three-dimensional surface renderings, topographical contour maps, contour maps, en-face color maps, and en-face grayscale maps.

Further, some embodiments related to retinal pathology provide clinicians with a cross-section of the pathology in the context of a map of the retina. For example, some embodiments provide a cross-section of a retinal abnormality presented in the context of a retinal thickness map. In some embodiments, two sequential scans of differing types (e.g., resolutions) are performed and simultaneously displayed, preferably on the same display. In some embodiments, the two display types are acquired using a single interaction with the user interface, say a single click or a single voice command.

Paunescu et al. ("Reproducibility of nerve fiber thickness, macular thickness, and optic nerve head measurements using StratusOCT" Invest Ophthalmol Vis Sci 45 (6) 1716-24, incorporated herein by reference in its entirety) describe methods of capturing a fundus image nearly "simultaneously" with the OCT, showing the location of the OCT beam on the retina. "Simultaneity", as used herein, simply means that data collection happens quickly enough that the side-by-side display of the two types of data are sufficiently synchronized that they present two views of the same object and structure. U.S. Pat. App. Pub. No. 2003/0199769 (incorporated herein by reference in its entirety), for example, suggests taking a Scanning Laser Ophthalmoscope (SLO) image point-by-point simultaneously with the OCT scan. This approach uses an additional imaging system consisting of a beam splitter and the SLO detector, and depends on hardware alignment between the OCT and SLO detectors. For the purpose of providing a fast fundus image, a Line Scanning Laser Ophthalmoscope (LSLO) is generally faster than the SLO and equally useful, as is the line-scan ophthalmoscope (LSO) of U.S. Patent Publication No. 2006/0228011, incorporated herein by reference in its entirety.

Various embodiments are related to visualization of images, e.g., to provide output to a user and to convey results of image analysis methods as described herein. For example, some embodiments provide information useful for live-time decisions and/or planning of clinical treatments, for analysis of previous clinical treatments (stents, drugs, genes, etc.), for similar purposes in preclinical studies, etc.

Automated segmentation results may be displayed in cross-sectional view or longitudinal view or en face view. In addition, images may be displayed in a three-dimensional view or a "fly-through" view. Different features may be displayed using different shading relative to one another or as different colors.

Quantification results may be displayed in an image view and/or reported in tables or text.

In some embodiments, surface and/or volume visualization techniques are used to provide views of the three-dimensional image data from any angle and, in some embodiments, with virtual lighting from any angle, in an interactive fashion. In some embodiments, such volumes are digitally sliced along any plane or arbitrary surface to create a reformatted two dimensional view.

Software for visualization and analysis of biological image data include those sold under the trade names of ParaView, ScanImage, μManager, MicroPilot, ImageJ, Vaa3D, ilastik (which includes machine learning, e.g., to aid a user in identifying image features), CellProfiler, CellExplorer, BrainExplorer, Zen (Zeiss), Amira (VSG), Imaris (Bitplane), ImagePro (Me diaCybernetics), Neurolucida (MBF Bioscience), LabVIEW (National Instruments), MATLAB (Mathworks), and Virtual Finger (see, e.g., Peng et al (2014) Nature Communications 5: 4342). See also, Walter et al (2010) Nature Methods 7: S26-S41; Eliceiri et al (2013) Nature Methods 9: 697; and Long (2012) PLoS Computational Biology 9: e1002519, each incorporated herein in its entirety. Further, in some embodiments the technology incorporates an image analysis library such as VTK, ITK, OpenCV, or the Java ImgLib.

Methods

Provided herein are embodiments of methods for processing and analyzing OCT image data. In some embodiments, the methods provide one or more measurements (e.g., distance, area, and/or volume measurements; e.g., measurements in one, two, or three dimensions, and, in some embodiments, measurements in one, two, or three dimensions as a function of time) Accordingly, in some embodiments the methods provide a technology to monitor changes is the size, location, and/or shape of lesions of the retina, layers of the retina, subretinal tissue, and RPE. For example, particular embodiments relate to a method for determining the area and/or volume of a region of interest within a biological tissue using an image produced by optical coherence tomography. The method comprises producing, acquiring, analyzing, displaying, manipulating, etc. three-dimensional OCT data and producing, acquiring, analyzing, displaying, manipulating, etc. two-dimensional "fundus" OCT data. For example, the three-dimensional OCT data provide a three-dimensional image of the biological tissue comprising the region of interest and the two-dimensional OCT data are fundus image data of the biological tissue comprising the region of interest.

In some preferred embodiments, the two-dimensional fundus data are associated with (e.g., registered with, linked to, etc.) the three-dimensional image of the biological tissue. In some embodiments, user interaction with the two-dimensional image data (e.g., analyzing, displaying, manipulating, etc. the two-dimensional image data) produces a linked, associated, coordinated interaction (e.g., analysis, display, manipulation, etc.) of the three-dimensional image data. For example, in some embodiments, methods comprise display of the two-dimensional fundus data and user interaction with the display of the two-dimensional fundus data. Then, in some embodiments, a user interacts with the two-dimensional fundus data—e.g., the user interacts with the display of the two-dimensional fundus data by use of an input device, e.g., a touch screen, mouse, track ball, etc. to provide a boundary around the region of interest and the user receives sensory feedback, e.g., the boundary is displayed superimposed on the two-dimensional fundus image data as the user interacts with the displayed image. Further, indication of the boundary around the region of interest in the two-dimensional fundus image provides an associated, coordinated boundary around the region of interest in the three-dimensional image data. In this way, the user, "draws" the boundary around the region of interest using the technology provided herein, e.g., using a combination of the OCT image data (e.g., the three-dimensional image data and associated two-dimensional fundus image data), an output device (e.g., display), an input device (e.g., a touch screen), and a computer configured to calculate the area and/or volume of a region of interest according to the methods and technologies described herein.

In some embodiments, user interaction with the three-dimensional OCT data (e.g., analyzing, displaying, manipulating, etc. the three-dimensional OCT data) produces a linked, associated, coordinated interaction (e.g., analysis, display, manipulation, etc.) of the two-dimensional fundus data. For example, in some embodiments, methods comprise display of the three-dimensional OCT data and user interaction with the display of the three-dimensional OCT data (e.g., examination of one or more "slices" of the three-dimensional OCT data, by "fly-through" of the OCT data, or by otherwise examining the three-dimensional OCT data on a display). Then, in some embodiments, a user interacts with the three-dimensional OCT data—e.g., the user interacts with the display of the three-dimensional OCT data by use of an input device, e.g., a touch screen, mouse, track ball, etc. to provide a boundary around the region of interest and the user receives sensory feedback, e.g., the boundary is displayed superimposed on the three-dimensional OCT data and/or on the two-dimensional fundus image data as the user interacts with the displayed image. Further, indication of the boundary around the region of interest in the three-dimensional OCT image provides an associated, coordinated boundary around the region of interest in the two-dimensional image data. In this way, the user, "draws" the boundary around the region of interest using the technology provided herein, e.g., using a combination of the OCT image data (e.g., the three-dimensional image data and associated two-dimensional fundus image data), an output device (e.g., display), an input device (e.g., a touch screen), and a computer configured to calculate the area and/or volume of a region of interest according to the methods and technologies described herein.

In some embodiments, a user provides a continuous boundary around the region of interest. In some embodiments a user provides a discontinuous boundary (e.g., a series of points, dots, lines, line segments (e.g., straight line segments, curved line segments), etc.) marking some of the region of interest (e.g., marking one or more locations of the edge of the region of interest). In some embodiments, a user provides points or portions of a boundary around a region of interest and an automated image processing algorithm completes the boundary using image analysis and the user-defined points or partial boundary to complete the boundary (e.g., using interpolation analysis to connect the user-provided portions of the boundary).

In embodiments of the technology in which the images are segmented, the technology is not limited by how the images are segmented. For example, various embodiments provide for the automated segmentation of the images (e.g., by computer algorithm that identifies image segments), semi-automated segmentation, or manual segmentation of the image (e.g., by a user who identifies image segments). See also, U.S. Pat. No. 8,811,745 (incorporated herein by reference), which describes systems and methods for segmentation and identification of structured features in images (e.g., an ocular image showing layered structures or other features of the retina). Some embodiments further provide for automated detection and identification (e.g., marking) of biological features in images such as, e.g., blood vessels. See, e.g., U.S. Pat. No. 8,750,615 (incorporated herein by reference in its entirety), which describes a system and related methods for automatic or semi-automatic segmentation and quantification of blood vessel structure and physiology, including segmentation, quantification, and visualization of vessel walls, plaques, and macrophages.

The image processing technology provides in particular a method for measuring a linear distance, an area, and/or a volume of a region of interest within a biological tissue using an image produced by optical coherence tomography. In an exemplary embodiment, an OCT apparatus (e.g., a SD-OCT apparatus) and a tissue are positioned for acquisition of OCT data (e.g., OCT image data such as, e.g., SD-OCT image data comprising three-dimensional image data and a fundus image). See, e.g., FIG. 1 showing an OCT apparatus ("OCT") and a sample (e.g., a tissue) in a schematic drawing. After acquiring OCT data (e.g., three dimensional OCT image data), the data are segmented to produce an image showing the segments (e.g., representing tissue layers and/or other features of the sample). For example, FIG. 2A (bottom panel) shows a projection of three-dimensional OCT data (e.g., an image as shown on a display such as, e.g., a computer screen) in two dimensions (e.g., a cross-section in a plane parallel, effectively parallel, and/or substantially parallel to the z-axis). The example OCT image in FIG. 2A (bottom panel) has been segmented (see, e.g., upper and lower lines corresponding to a first segment and a second segment), e.g., to show tissue layers. Further, the exemplary OCT image shown in FIG. 2A (bottom panel) comprises a region of interest as a protrusion in the upper segment. In exemplary embodiments, such a protrusion may indicate abnormal tissue growth, a lesion (a retinal lesion), central neovascularization (e.g., associated with macular degeneration) or other abnormal feature in a biological tissue. Also shown in FIG. 2A (upper panel) is an exemplary OCT fundus image (e.g., as shown on a display such as, e.g., a computer screen) in a plane normal, effectively normal, and/or substantially normal to the z-axis (e.g., in the x-y plane). The exemplary fundus image shown in FIG. 2A (upper panel) shows the region of interest (FIG. 2A (upper panel), black outlined shape).

Figure 2A:
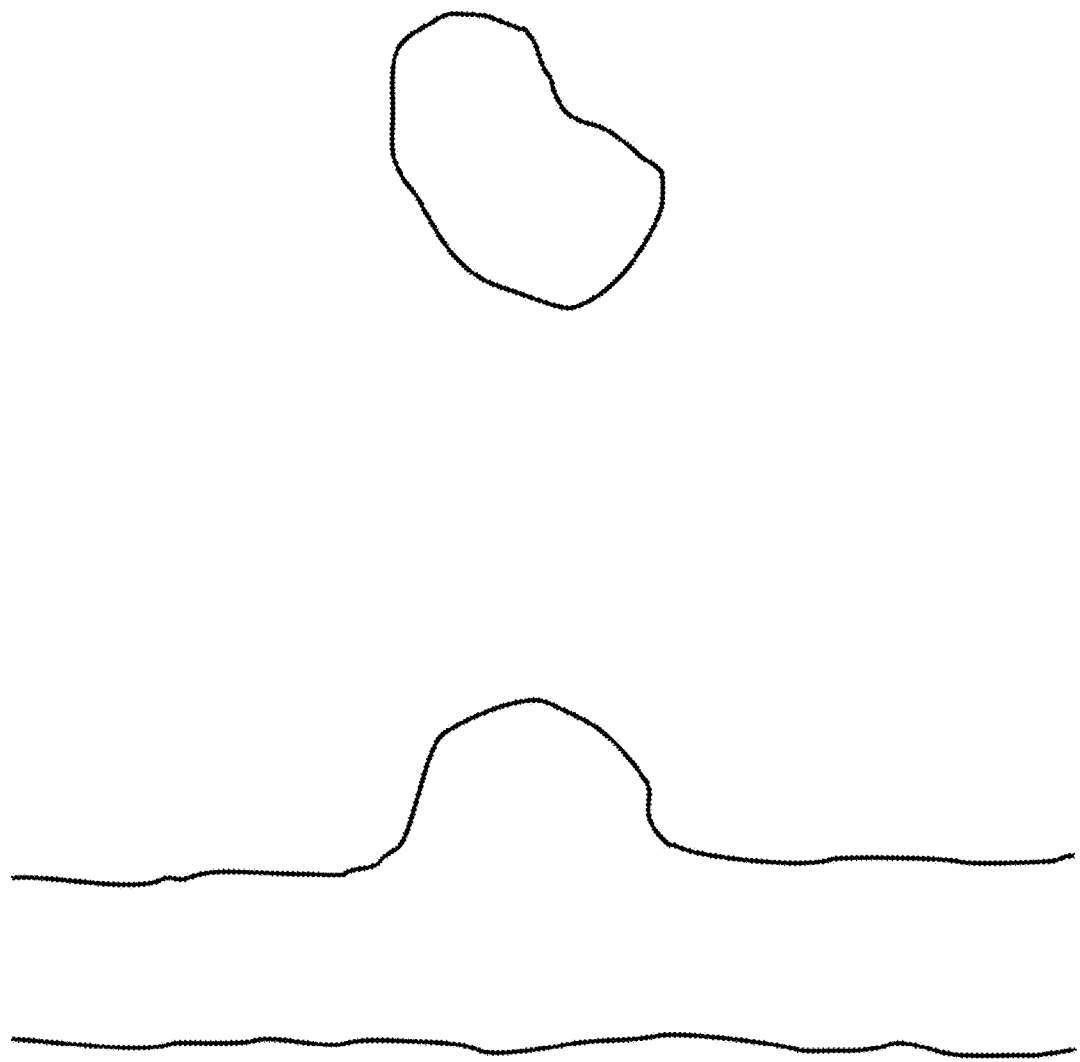
FIG. 2A is a schematic drawing showing a cross-section image of a region of interest in a segmented image of a tissue sample (lower panel) and the associated fundus image showing the region of interest (upper panel). The lower panel shows a first segment and a second segment as an upper black line and a lower black line. The upward protrusion in the upper black line represents a growth abnormality, lesion, etc., or other region of interest of a sample.

According to embodiments of the technology provided herein, the images are analyzed to determine the area and/or volume of the region of interest (e.g., the protrusion shown in FIG. 2A (bottom panel)).

In some embodiments, the greatest linear dimension of the region of interest is determined (e.g., by examination of the fundus image and/or the three dimensional OCT data (e.g., image)). See FIG. 2B (upper panel), g. The greatest linear dimension is the greatest distance across the region of interest. For example, the greatest linear dimension can be determined by identifying the longest line segment having each of its two ends touching the perimeter of the region of interest. In some embodiments, the greatest linear dimension of the region of interest is provided by a user. In particular, in some embodiments the fundus image is provided to a user on a display and the user draws a line segment having each of its two ends touching the perimeter of the region of interest using a computer and computer input device (e.g., mouse, touch screen, light pen, etc.). As the user draws the line segment, the line segment is provided on the fundus image of the region of interest on the display. In some embodiments, a computer determines and provides the greatest linear dimension of the region of interest (e.g., by identifying the longest line segment having each of its two ends touching the perimeter of the region of interest). In some embodiments, the computer displays a line on a display showing the greatest linear dimension of the region of interest.

In some embodiments, a boundary is provided around the region of interest, e.g., an area enclosing the region of interest is identified in the fundus image. For example, in some embodiments a circle having a diameter (see, e.g., FIG. 2B (top panel), d) greater than or equal to the greatest linear dimension g is provided to circumscribe the region of interest. The boundary has an area A (see, e.g., FIG. 2B (top panel), grey region) and the region of interest is within the area A.

In embodiments in which the boundary is a circle, the area $A = \Pi \times (d/2)^2$.

The technology is not limited in the shape of the boundary. The boundary may be any shape (e.g., circle, ellipse, square, etc., or an irregular shape) enclosing the region of interest and having an area. See, e.g., FIG. 2D-1 (showing a circle boundary) and FIG. 2D-2 (showing an irregular boundary). In some embodiments, a computer determines the boundary. In some embodiments, a user determines the boundary. For example, in some embodiments the fundus image is provided to a user on a display and the user draws a shape enclosing the region of interest using a computer and computer input device (e.g., mouse, touch screen, light pen, etc.). As the user draws the boundary, the boundary is provided on the fundus image of the region of interest on the display. In preferred embodiments, the area A of the boundary is determined by computer analysis, e.g., according to algorithms for determining the area of shapes (e.g., irregular shapes).

Figure 2B:
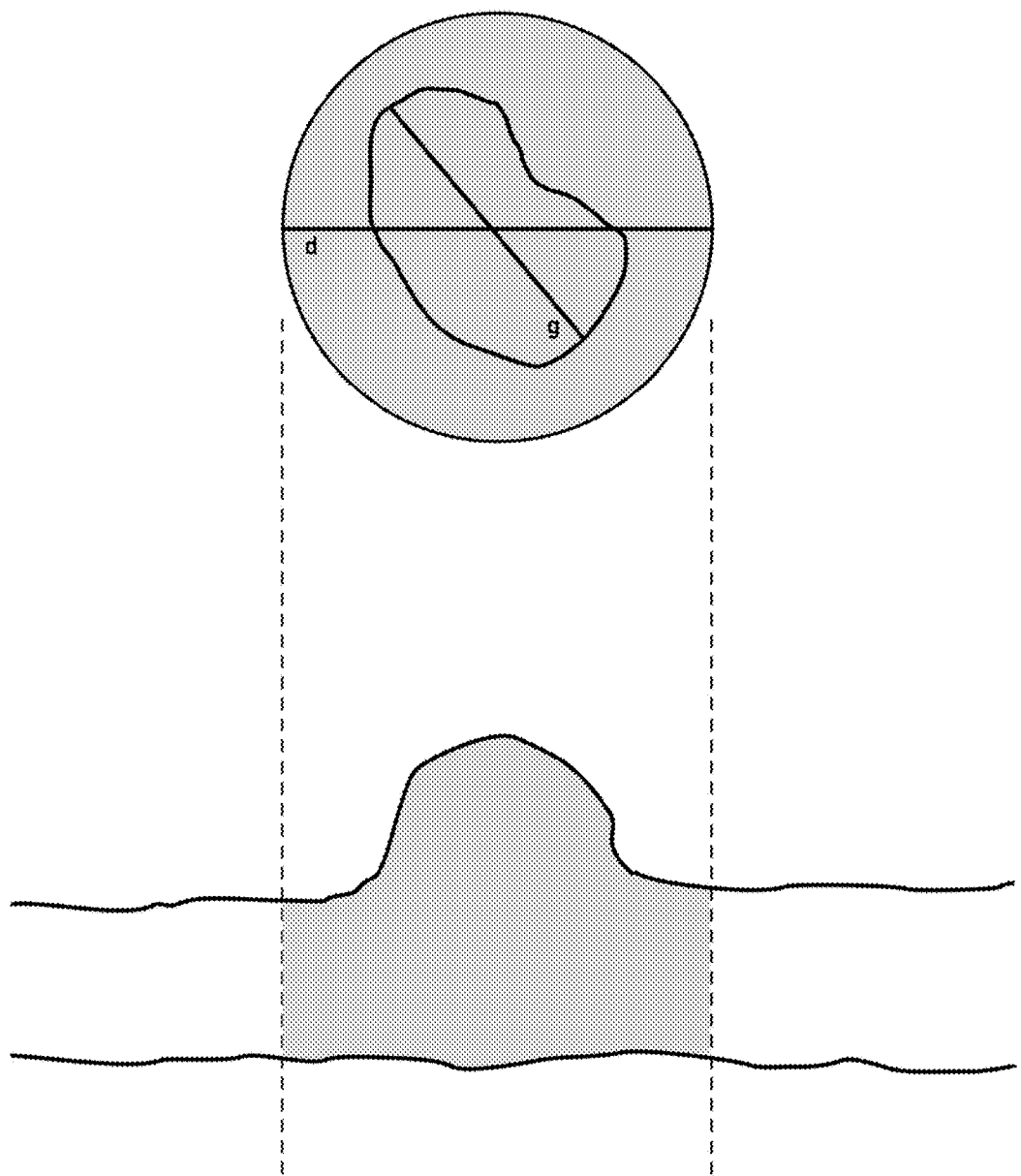
FIG. 2B is a schematic drawing showing a boundary provided around the region of interest in the fundus image (upper panel). The region of interest has a greatest linear dimension g and, in some embodiments, the boundary is a circle having a diameter d. The boundary defines an area A (upper panel, grey region). Extension of the boundary through the image to cross the segments defines a volume v enclosed by the first segment, second segment, and extended boundary (lower panel, grey region).

Extension of the boundary substantially in the direction of the z-axis (e.g., through the sample (e.g., tissue)) defines a volume v in the three dimensional OCT data (e.g., image). The volume v is defined by the first and second segments and by extension of the boundary through the segments. FIG. 2B (bottom panel), grey region, shows a cross-section of the volume defined by the first segment, second segment, and the extended boundary. Computer analysis of the three dimensional data (e.g., image data) provides a volume v of the volume defined by the first segment, second segment, and the extended boundary.

The data are analyzed to determine a distance t (e.g., thickness) between the first segment and the second segment in the direction of the z-axis. In particular embodiments, t is the average distance between the first segment and the second segment measured along the perimeter of the boundary. In alternative embodiments, the distance t may also be the maximum distance between the first segment and the second segment measured along the perimeter of the boundary, the minimum distance between the first segment and the second segment measured along the perimeter of the boundary, and/or any other distance calculated between the first segment and the second segment measured along the perimeter of the boundary. Average distance may be calculated using an average calculated in a sliding window moved along the perimeter of the boundary. The distance t provides a measurement for the normal distance between the first segment and the second segment in a normal sample (e.g., a normal tissue), e.g., a sample that does not comprise abnormal growth, does not comprise a lesion, etc. As such, preferred embodiments are those in which the boundary is provided in a region of the data (e.g., images) corresponding to healthy, normal sample (e.g., healthy, normal tissue), e.g., healthy, normal, etc. relative to the region of interest, which corresponds to abnormal sample (e.g., abnormal tissue comprising a feature such as a lesion).

Figure 2C:
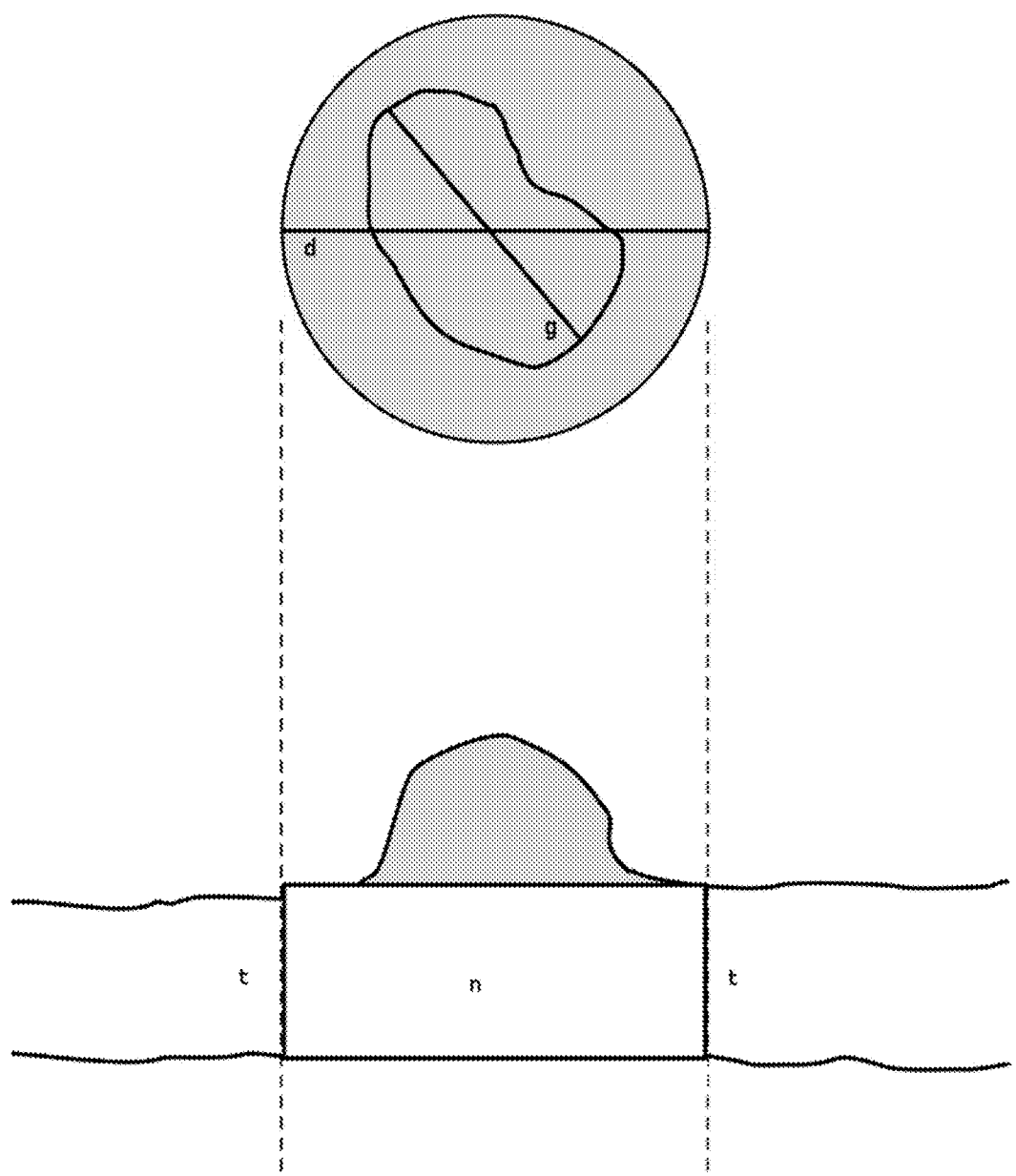
FIG. 2C is a schematic drawing showing a volume n (white region) in cross-section, calculated from the area A and the distance t (e.g., an average thickness between the first segment and the second segment calculated around the perimeter of the boundary) as described herein. The volume V of the region of interest is shown in the lower panel in grey.

The technology provides methods for calculating the area A and/or the volume V of a region of interest (e.g., an abnormality, lesion, etc.). Thus, in some embodiments, the area A defined by the boundary and the distance t are used to calculate a volume n. The volume n is subtracted from the volume v determined above to provide the volume V of the region of interest (e.g., abnormality, lesion, etc.). Accordingly, the volume n is calculated as the product of the area A of the boundary and the thickness t, as determined above. FIG. 2C (lower panel) shows a volume n in cross-sectional view (white rectangle). The volume n has a height that is the distance t. The top and bottom of the volume n each have an area A. Accordingly, the volume V of the region of interest (FIG. 2C (lower panel), grey region) is calculated by subtracting the volume n (FIG. 2C (lower panel), white region) from the volume v (FIG. 2B (lower panel), grey region).

Figure 2D:
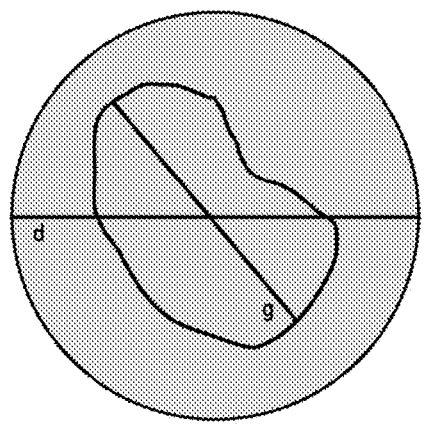
FIG. 2D is a schematic showing embodiments of the technology comprising providing a circular boundary having an area A (FIG. 2D-1) and providing an irregularly shaped boundary having an area A (FIG. 2D-3).
Figure 2D:
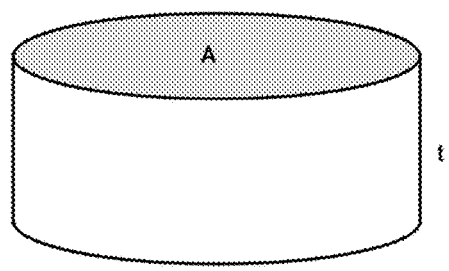
Figure 2D:
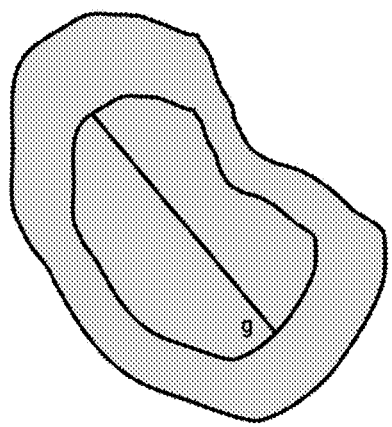
Figure 2D:
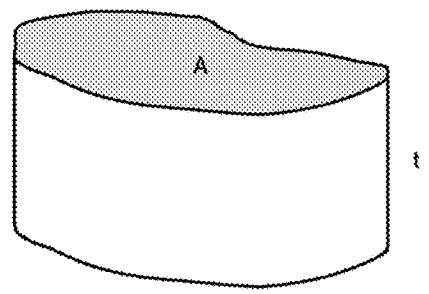

While certain embodiments are described above using a boundary that is a circle, the technology comprises use of a boundary of any shape (e.g., circle, ellipse, square, etc., or an irregular shape) enclosing the region of interest and having an area A. For example, FIG. 2D-1 and FIG. 2D-2 show a volume n having a top and bottom that are circles having area A and height t. FIG. 2D-3 and FIG. 2D-4 show a volume n having a top and bottom that are an irregular shape having area A and height t.

In some embodiments, the area A is determined from examining the three-dimensional OCT image to localize the margins of the area on the two-dimensional image. For example, in some embodiments, area A is calculated from the interpolation of points on the edges of the area using a three-dimensional image that is registered with the two-dimensional image.

Accordingly, the technology provides a general method for determining the area A and/or the volume V of a region of interest in OCT data, e.g., comprising the steps of acquiring OCT data, determining the volume v (e.g., defined by the first and second segments and by the extension of the boundary through the segments), calculating the volume n (e.g., as the product of the area A of the boundary and the distance t), and subtracting n from v.

Systems

Some embodiments of the technology provide systems determining the area and/or the volume of a region of interest in OCT data (e.g., in OCT data acquired from a biological tissue, e.g., OCT image of a biological tissue such as a retina). Systems according to the technology comprise, e.g., an OCT apparatus (e.g., a SD-OCT apparatus), a computer, and software to instruct a computer to perform a method as described herein. Some embodiments further comprise a display (e.g., to provide three dimensional OCT data (e.g., three dimensional OCT images) and/or two dimensional OCT data (e.g., a fundus image) to a user) and an input device (e.g., for a user to provide information to the computer (e.g., to provide a boundary enclosing a region of interest).

For example, in some embodiments, computer-based analysis is used to calculate the area A of the boundary, determine the distance t between the first segment and the second segment, calculate the volume v (e.g., defined by the first segment, second segment, and the boundary extended through the segments), and the volume n (e.g., product of area A and distance t), and volume V (volume of the region of interest). In some embodiments, one or more of these calculations use data provided by a user and/or data acquired by the computer.

For instance, some embodiments comprise a computer system upon which embodiments of the present technology may be implemented. In various embodiments, a computer system includes a bus or other communication mechanism for communicating information and a processor coupled with the bus for processing information. In various embodiments, the computer system includes a memory, which can be a random access memory (RAM) or other dynamic storage device, coupled to the bus, and instructions to be executed by the processor. Memory also can be used for storing temporary variables or other intermediate information during execution of instructions to be executed by the processor. In various embodiments, the computer system can further include a read only memory (ROM) or other static storage device coupled to the bus for storing static information and instructions for the processor. A storage device, such as a magnetic disk or optical disk, can be provided and coupled to the bus for storing information and instructions.

In various embodiments, the computer system is coupled via the bus to a display, such as a cathode ray tube (CRT) or a liquid crystal display (LCD), for displaying information to a computer user (e.g., three dimensional OCT images and/or two dimensional OCT images such as a fundus image).

An input device, including alphanumeric and other keys, can be coupled to the bus for communicating information and command selections to the processor. Another type of user input device is a cursor control, such as a mouse, a trackball, a light pen, a touch screen, or cursor direction keys, for communicating direction information and command selections to the processor and for controlling cursor movement on the display (e.g., to draw shapes, lines, etc. to show on the computer display). This input device typically has two degrees of freedom in two axes, a first axis (e.g., x) and a second axis (e.g., y), that allows the device to specify positions in a plane. These x and y axes are not necessarily coincident with the x and y axes shown in FIG. 1 (e.g., with respect to the sample and images).

A computer system can perform embodiments of the present technology. Consistent with certain implementations of the present technology, results can be provided by the computer system in response to the processor executing one or more sequences of one or more instructions contained in the memory. Such instructions can be read into the memory from another computer-readable medium, such as a storage device. Execution of the sequences of instructions contained in the memory can cause the processor to perform the methods described herein. Alternatively, hard-wired circuitry can be used in place of or in combination with software instructions to implement the present teachings. Thus, implementations of the present technology are not limited to any specific combination of hardware circuitry and software.

The term "computer-readable medium" as used herein refers to any medium or media that participates in providing instructions to the processor for execution. Such a medium can take many forms, including but not limited to, non-volatile media, volatile media, and transmission media. Examples of non-volatile media can include, but are not limited to, optical or magnetic disks, such as a storage device. Examples of volatile media can include, but are not limited to, dynamic memory. Examples of transmission media can include, but are not limited to, coaxial cables, copper wire, and fiber optics, including the wires that comprise the bus.

Common forms of computer-readable media include, for example, a floppy disk, a flexible disk, hard disk, magnetic tape, or any other magnetic medium, a CD-ROM, any other optical medium, punch cards, paper tape, any other physical medium with patterns of holes, a RAM, PROM, and EPROM, a FLASH-EPROM, any other memory chip or cartridge, or any other tangible medium from which a computer can read.

Various forms of computer readable media can be involved in carrying one or more sequences of one or more instructions to the processor for execution. For example, the instructions can initially be carried on the magnetic disk of a remote computer. The remote computer can load the instructions into its dynamic memory and send the instructions over a network connection (e.g., a LAN, a WAN, the internet, a telephone line). A local computer system can receive the data and transmit it to the bus. The bus can carry the data to the memory, from which the processor retrieves and executes the instructions. The instructions received by the memory may optionally be stored on a storage device either before or after execution by the processor.

In accordance with various embodiments, instructions configured to be executed by a processor to perform a method are stored on a computer-readable medium. The computer-readable medium can be a device that stores digital information. For example, a computer-readable medium includes a compact disc read-only memory (CD-ROM) as is known in the art for storing software. The computer-readable medium is accessed by a processor suitable for executing instructions configured to be executed.

In accordance with such a computer system, some embodiments of the technology provided herein further comprise functionalities for collecting, storing, and/or analyzing data (e.g., OCT images, e.g., three dimensional OCT images, two dimensional OCT images). For example, some embodiments contemplate a system that comprises a processor, a memory, and/or a database for, e.g., storing and executing instructions, analyzing image data, performing calculations using the data, transforming the data, and storing the data. It some embodiments, an algorithm applies a model for calculating (e.g., approximating) an area and/or a volume in the image data. Some embodiments provide for the resizing, cropping, flattening, or other manipulation of image data. Particular embodiments provide a database to organize, search, process, analyze, share and visualize image data and image metadata.

In some embodiments, area and/or volume data (e.g., comprising information relating to the area A and/or volume V of a region of interest for a subject) are stored (e.g., associated with a time at which the area A and/or volume V is determined and/or associated with the particular subject. For example, volume data (e.g., comprising information relating to the area A and/or volume V of a region of interest for a subject) are acquired at more than one time (e.g., over a period of days, weeks, months, years, or decade) and an area A (e.g., $A_1$) and/or a volume V (e.g., $V_1$) acquired at one time is compared to an area A (e.g., $A_2$) and/or a volume V (e.g., $V_2$) acquired at another time. In some embodiments, the difference in the two values of A (e.g., $A_2-A_1$) and/or V (e.g., $V_2-V_1$) is used to inform a treatment of the subject. For example, in some embodiments the magnitude of the area $A_1$ and/or volume $V_1$ acquired at one time is used to determine a treatment, dosage, pharmaceutical administration, medical intervention (e.g., surgery), etc. Then, determining the area $A_2$ and/or volume $V_2$ at a later time provides an indication of the effectiveness of the treatment, e.g., in some embodiments an $A_2$ and/or a $V_2$ that is less than $A_1$ and/or $V_1$ for the region of interest indicates that the treatment was effective.

Many diagnostics involve determining the presence of, size of, location of, etc. a region of interest in a sample. Thus, in some embodiments, an equation comprising variables representing the presence of, size of, location of, etc. a region of interest in a sample produces a value that finds use in making a diagnosis or assessing the presence or qualities of a region of interest. As such, in some embodiments this value is presented by a device, e.g., by an indicator related to the result (e.g., an LED, an icon on a display, a sound, or the like). In some embodiments, a device stores the value, transmits the value, or uses the value for additional calculations.

Thus, in some embodiments, the present technology provides the further benefit that a clinician, who is not likely to be trained in image analysis, pathology, and/or the biology of particular tissues need not understand the raw data. The data are presented directly to the clinician in its most useful form. The clinician is then able to utilize the information to optimize the care of a subject. The present technology contemplates any method capable of receiving, processing, and transmitting the information to and from laboratories conducting the assays, information providers, medical personal, and/or subjects. For example, in some embodiments of the present technology, data are acquired from analyzing a subject's tissue and the data are submitted to an analysis service (e.g., a clinical lab at a medical facility, a tissue profiling business, etc.), located in any part of the world (e.g., in a country different than the country where the subject resides or where the information is ultimately used). For example, the subject may visit a medical center to be tested and to have data sent to the profiling center. Where the data comprises previously determined biological information, the information may be directly sent to the profiling service by the subject (e.g., data transmitted to a computer of the profiling center using electronic communication systems). Once received by the profiling service, the data are processed and a profile is produced that is specific for the diagnostic or prognostic information desired for the subject. The profile data are then prepared in a format suitable for interpretation by a treating clinician. For example, rather than providing raw image data, the prepared format may represent a diagnosis or risk assessment for the subject, along with recommendations for particular treatment options. The data may be displayed to the clinician by any suitable method. For example, in some embodiments, the profiling service generates a report that can be printed for the clinician (e.g., at the point of care) or displayed to the clinician on a computer display. In some embodiments, the information is first analyzed at the point of care or at a regional facility. The raw data are then sent to a central processing facility for further analysis and/or to convert the raw data to information useful for a clinician or patient. The central processing facility provides the advantage of privacy (all data are stored in a central facility with uniform security protocols), speed, and uniformity of data analysis. The central processing facility can then control the fate of the data following treatment of the subject. For example, using an electronic communication system, the central facility can provide data to the clinician, the subject, or researchers. In some embodiments, the subject is able to access the data using the electronic communication system. The subject may chose further intervention or counseling based on the results. In some embodiments, the data are used for research use. For example, the data may be used to further optimize the inclusion or elimination of markers as useful indicators of a particular condition associated with a disease.

Applications

OCT is widely used, for example, to obtain high-resolution images of the anterior segment of the eye and the retina. As such, the technique finds use, for example, in assessing axonal integrity in diseases such as, e.g., multiple sclerosis, other neurodegenerative diseases, and glaucoma. OCT finds use for monitoring the progression of glaucoma and to image coronary arteries to detect lipid-rich plaques. In an exemplary use, the technology finds use in measuring retinal thickness. Retinal thickness may be abnormally large in cases of retinal edema or traction by membranes in the vitreous humor. On the other hand, the retina and/or RFE may appear thin or absent in cases of atrophic degeneration, chorioretinitis, or trauma to the retina. Meanwhile, changes in retinal thickness may be localized or extend over large areas. In certain cases, the overall contour of the retina may become abnormal. For example, pronounced myopia, particularly due to posterior staphylomas, may create a highly concave retina. Retina layers overlying regions of RPE atrophy may become markedly thinned or lost. Detachment of the retinal pigment epithelium (RPE), subretinal cysts, or subretinal tumors may produce a relative convexity of the retina. Therefore, mapping the retina contour or retinal thickness makes it possible to determine the extent and severity of such conditions and to monitor progress of treatment.

In addition, the technique finds use in imaging brain tissue in vivo, e.g., using OCT to produce detailed images of mice brains through a transparent zirconia window implanted in the skull. OCT finds use to identify root canals in teeth (e.g., canal in the maxillary molar). Also, OCT finds use in interventional cardiology to diagnose coronary artery disease.

Furthermore, OCT finds use in industrial applications, such as in non-destructive testing (NDT), material thickness measurements, and for examining thin silicon wafers and compound semiconductor wafers (e.g., to make thickness measurements, surface roughness characterization, surface imaging, cross-section imaging, and volume loss measurements). OCT systems with feedback can be used to control manufacturing processes. OCT finds use in the pharmaceutical industry to control the coating of tablets.

In some embodiments, the technology finds use in metric analysis of a CNV lesion complex and/or a region of RPE loss, e.g., as associated with macular degeneration, in OCT (e.g., SD-OCT) images (see, e.g., Examples 2 and 3).

Although the disclosure herein refers to certain illustrated embodiments, it is to be understood that these embodiments are presented by way of example and not by way of limitation.

EXAMPLES

Prophetic Example 1

In some embodiments, the technology finds use in diagnosing and treating a patient. For example, the technology aids a physician who determines that a patient has a subretinal choroidal neovascular membrane with subretinal fluid developing in the macula of an eye. A volumetric raster OCT scan of a 6 mm×6 mm region of the central macula is obtained (e.g., using default settings) to capture the 3D image. The OCT scan is registered to a retinal angiographic image obtained during the same visit. The physician determines the boundaries of the lesion in the fundus angiogram image. Using a computer mouse, the user defines a region that includes the lesion but extends beyond it into retinal tissue that appears normal, thereby defining the area A for analysis. The defined region happens to be irregular in shape (e.g., not perfectly circular). The segmentation algorithm is run, which segments the internal limiting membrane layer and the retinal pigment epithelium layer of the retina. The volume of the defined region of interest is calculated. From this the volume of the abnormality, $V_1$, is calculated by the software. This volume $V_1$ is 1.5 mm$^3$. At this first visit, the patient is given a drug treatment to treat the lesion. At a second visit, the scan and angiogram studies are repeated on the patient's eye and the data are registered with software. Again, the physician identifies the region of interest and draws on the angiogram image the region of interest that circumscribes the lesion and some normal retina, which is not circular. After the segmentation algorithm is run, a second volume from the second visit is obtained. From this, $V_2$ is calculated. $V_2$ is determined to be 0.75 mm$^3$. The ratio $V_2/V_1$ is 0.5. The physician determines that the treatment has lessened the volume of the abnormality by 50%, indicating a treatment effect. The physician plans to continue treatment with administration of the same drug at the second visit due to a good initial response to treatment.

Example 2

Metric Analysis of a CNV Lesion

Quantitative analysis of OCT data has been used in clinical trials targeting wet AMD in patients. In one class of treatments comprising administration of anti-VEGF agents (e.g., Lucentis, Eylea), metric evaluation of retinal thickness is used to monitor subretinal fluid accumulation. In addition, combination therapies targeting VEGF and PDGF find use in treatment of patients. In these treatments, metric assessment (e.g., measurement of the volume and/or area) of CNV is used to monitor the effectiveness of the PDGF treatment. Accordingly, the technology described herein finds use in the quantitative analysis (e.g., metric analysis (e.g., determination of volume and/or area)) of CNV size based on SD-OCT.

In an exemplary application of embodiments of the technology, an SD-OCT scan and an associated fundus image registered pixel-to-pixel to the SD-OCT data are provided. In some embodiments, the technology is based on the use of SD-OCT data only, but an improved technology is provided by use of SD-OCT data and an associated fundus image. For example, providing both OCT data and a registered fundus image improve user analysis and grading of the tissues and lesions in the patient. In some embodiments, the SD-OCT and fundus image are displayed on a display side by side, e.g., in a split view mode, e.g., as provided by a software implementation of the technology provided herein (see, e.g., FIG. 3A and FIG. 3B). In this view mode, the long horizontal white line in the fundus image of FIG. 3A marks the plane view of the OCT data displayed in FIG. 3B; and the location of the vertical white tick mark on the fundus image (FIG. 3A) is correlated to the location of the two vertical white tick marks on the OCT image (FIG. 3B).

Figure 3A:
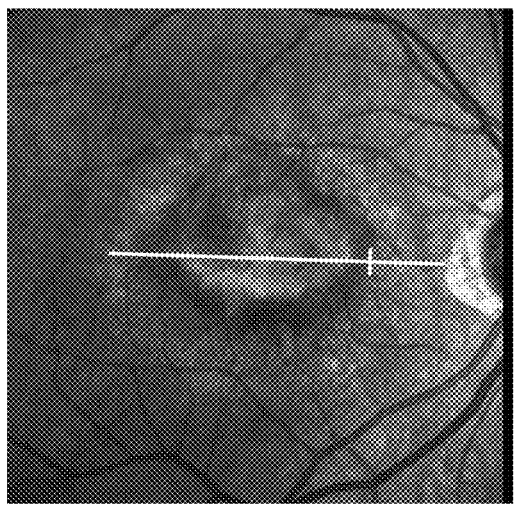
FIG. 3A shows a fundus image and FIG. 3B shows an associated view of OCT data. The long horizontal white line in the fundus image of FIG. 3A marks the plane view of the OCT data displayed in FIG. 3B. The location of the vertical white tick mark on the fundus image (FIG. 3A) is correlated to the location of the two vertical white tick marks on the OCT image (FIG. 3B).
Figure 3B:
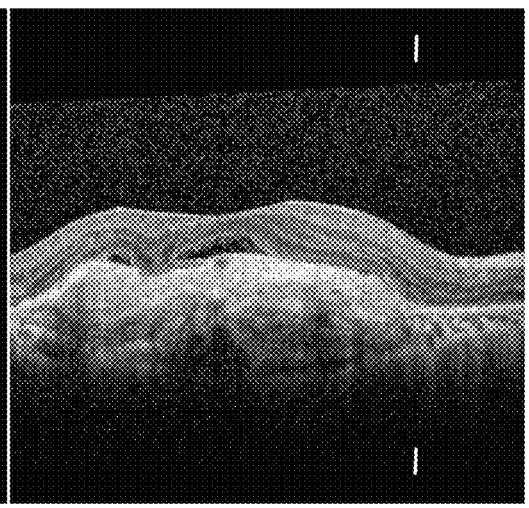

FIG. 3A shows a fundus image and FIG. 3B shows an associated view of OCT data. The fundus image and OCT scan show a CNV complex, which occupies approximately left three-quarters of the OCT image field in FIG. 3B (e.g., to the left of the white tick marks). The view of the OCT data shows thick, multi-layers of reflective materials that are packed together. The retina appears nearly normal in the right quarter of the OCT image (e.g., to the right of the white tick marks), where retinal pigment epithelium is visible and flat. The retinal pigment epithelium appears to be nearing a normal state at the left edge of the OCT data view shown. The left edge of the OCT image and the vertical tick marks in the OCT image mark the edges of the CNV lesion, e.g., in some embodiments a user marks the edge (e.g., boundary) of the CNV lesion and in some embodiments a method implemented in computer software marks the edge (e.g., boundary) of the CNV lesion.

Figures 4A, 4B:
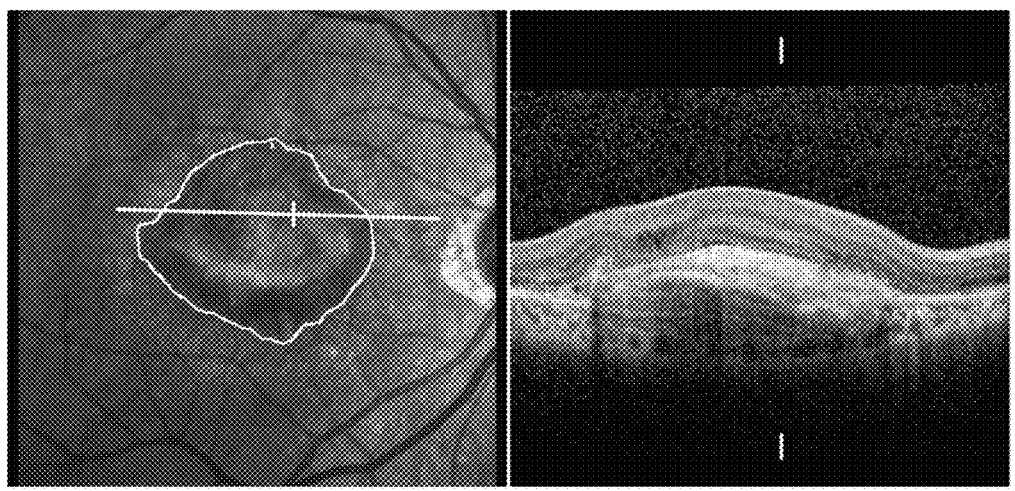
FIG. 4A shows a fundus image and FIG. 4B shows an associated view of OCT data obtained by imaging the retina of a subject. The long horizontal white line in the fundus image of FIG. 4A marks the plane view of the OCT data displayed in FIG. 4B. The location of the vertical white tick mark on the fundus image (FIG. 4A) is correlated to the location of the two vertical white tick marks on the OCT image (FIG. 4B). The region of interest encompassing a CNV lesion is outlined in white on FIG. 4A.
Figure 5A:
FIG. 5A shows a fundus image and FIG. 5B shows an associated view of OCT data obtained at another (e.g., later) time point by imaging the same area of the retina of the same subject from whom the image data in FIG. 4A and FIG. 4B were obtained. The long horizontal white line in the fundus image of FIG. 5A marks the plane view of the OCT data displayed in FIG. 5B. The location of the vertical white tick mark on the fundus image (FIG. 5A) is correlated to the location of the two vertical white tick marks on the OCT image (FIG. 5B). The region of interest encompassing a CNV lesion is outlined in white on FIG. 5A.
Figure 5B:

Accordingly, using embodiments of the technology provided herein, a user explores the OCT (e.g., SD-OCT) scan and/or fundus image to locate the edge of the CNV lesion. As the user evaluates the image(s) and identifies the edge of the CNV lesion, the user marks the edge of the lesion on the fundus photo. Then, in some embodiments, after exploring the OCT (e.g., SD-OCT) data set, the user identifies (e.g., traces, marks) the area encompassing the extent of the CNV lesion. Alternatively, in some embodiments, software automatically determines and indicates the area encompassing the extent of the CNV lesion, e.g., in some embodiments software uses image analysis and one or more points, dots, line segments, etc. provided by the user identifying the edge of the lesion. See, e.g., FIG. 4A and FIG. 5A showing the areas marked on fundus images and the views of the registered OCT data in FIG. 4B and FIG. 5B. FIG. 4A and FIG. 4B are image data of a patient's retina acquired at a time point; FIG. 5A and FIG. 5B are image data of the same region of the same patient's retina at another (e.g., later) time point. The long horizontal white lines in the fundus images of FIG. 4A and FIG. 5A marks the plane view of the OCT data displayed in FIG. 4B and FIG. 5B, respectively; and the location of the vertical white tick mark on the fundus image (FIG. 4A and FIG. 5A) is correlated to the location of the two vertical white tick marks on the OCT images (FIG. 4B and FIG. 5B).

The area of the region of interest is then derived automatically according to the technology provided herein (e.g., by an algorithm to determine the area of the region of interest defined by the line encompassing the region of interest). After segmenting the image data, in some embodiments, the volume of the CNV lesion complex is calculated (e.g., by calculating the volume v within the boundary of area A and between the first segment and the second segment; calculating the average thickness t between the first segment and the second segment along the boundary (e.g., along the perimeter of area A); and calculating the volume V of the region of interest using $V=v-(t\times A)$).

In an exemplary use of the technology, a subject is enrolled in a treatment course and monitored by OCT imaging. At a visit, the area of a CNV lesion is 11.8 mm$^2$ or 4.64 disc area (see, e.g., FIG. 4A showing the size of a lesion prior to a treatment). At a later visit of the same subject, the area of the CNV lesion is reduced to 8.17 mm$^2$ or 3.21 disc area (see, e.g., FIG. 5A showing the size of the same region of the same patient after treatment). The reduction in the area of the region of interest (e.g., the smaller area of the region of interest in FIG. 5A relative to the area of the region of interest in FIG. 4A) indicates that the treatment is effective.

Example 3

Metric Analysis of a Region of RPE Loss

Figure 6A:
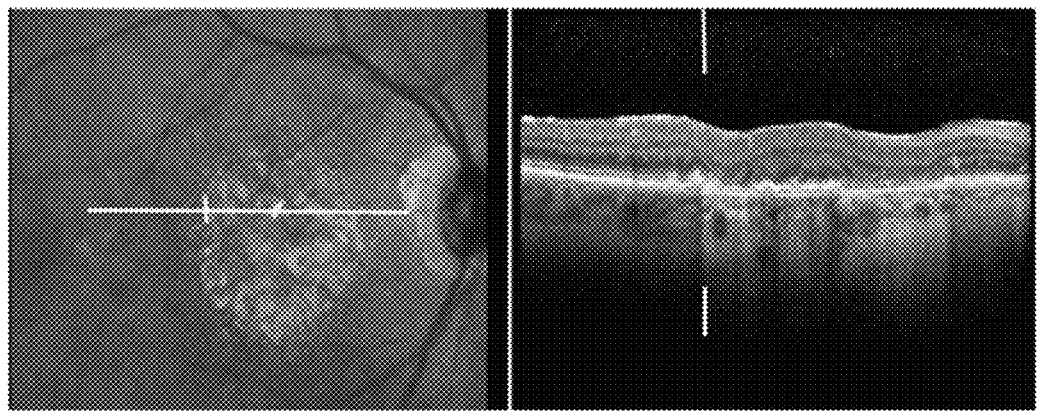
FIG. 6A shows a fundus image (left panel) and an associated view of OCT data (right panel) obtained by imaging the retina of a patient with AMD and GA. The horizontal white line on the fundus image corresponds to the OCT B scan shown. The white tick mark shows the corresponding location between the OCT image and the fundus image at the boundary between affected retina and RPE and relatively intact RPE/retina.
Figure 6B:
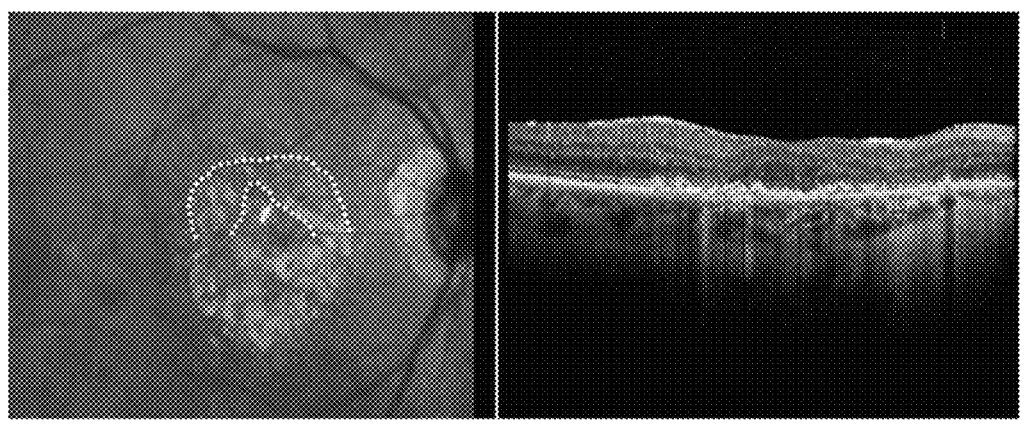
FIG. 6B shows fundus image (left panel) and the OCT image (right panel) from the same patient and visit whereby the boundaries of the atrophy have been identified on the OCT B scans and the corresponding locations are marked on the fundus image. The superior portion of the lesion has been analyzed in this image and the inferior portion has not yet been analyzed.
Figure 6C:
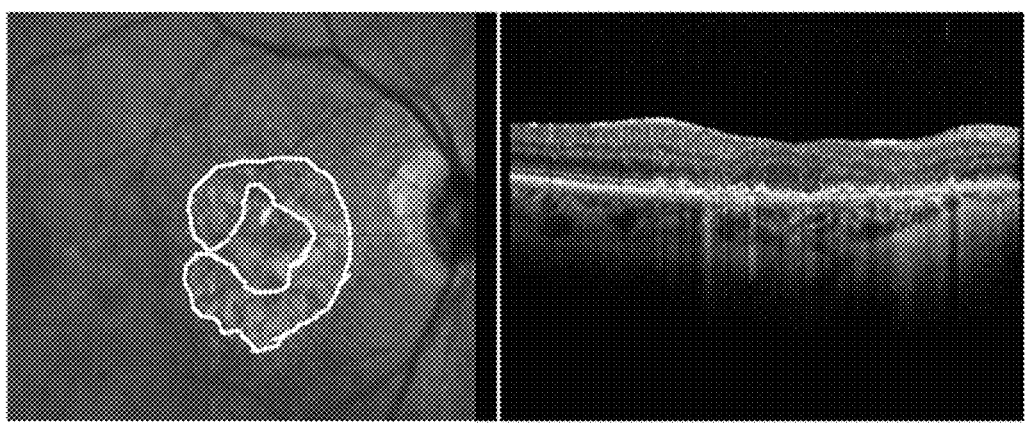
FIG. 6C shows that the analysis has been completed and the area of the GA has been completely circumscribed to define the region whereby the area A has been calculated.

The technology finds use in managing the care and treatment of a patient having AMD, e.g., to monitor vision defects and associated lesions of the retina and/or RPE. For example, during examination of the patient, OCT data are obtained from the patient's eye. The data show a complex region of RPE loss (see, e.g., FIG. 6A showing a B scan and an en face infrared image). A user scrolls through the stacked B scans in the 3D image to mark the border of the atrophy, e.g., because the structure of interest is not visible on, or not definitely located in, the en face image (FIG. 6B, showing the region of atrophy partially defined, using the boundary as the location where the layer of the external limiting membrane of the retina is lost). Finally, the boundary within the area of RPE loss is found (FIG. 6C, showing the completed circumscribed region of RPE loss). The region is calculated to have an area of 4.75 mm$^2$ and the distance of the nearest border of RPE lost to the foveal center is 150 microns.

Other useful metrics are provided by and/or calculated from parameters associated with the boundaries of regions of interest as defined with this methodology. For instance, metrics defining the shape of a lesion obtained from measurements described herein (e.g., from a measurement of the perimeter of the boundary of area A) have prognostic value in some embodiments of the technology (see, e.g., Domalpally (2013) "Circularity Index as a Risk Factor for the Progression of Geographic Atrophy" *Ophthalmology* 120 (12): 2666-71).

All publications and patents mentioned in the above specification are herein incorporated by reference in their entirety for all purposes. Various modifications and variations of the described compositions, methods, and uses of the technology will be apparent to those skilled in the art without departing from the scope and spirit of the technology as described. Although the technology has been described in connection with specific exemplary embodiments, it should be understood that the invention as claimed should not be unduly limited to such specific embodiments. Indeed, various modifications of the described modes for carrying out the invention that are obvious to those skilled in the art are intended to be within the scope of the following claims.

I claim:

1. A method of treating a subject having a tissue abnormality, the method comprising:
    a) acquiring an area and/or a volume of the tissue abnormality by:
        i) acquiring three-dimensional OCT data comprising at least a first segment and a second segment comprising the tissue abnormality;
        ii) acquiring two-dimensional image data comprising the tissue abnormality, wherein the tissue abnormality in the three-dimensional OCT data corresponds to the tissue abnormality in the two-dimensional data;
        iii) drawing a boundary around the tissue abnormality in the two-dimensional image data, the boundary enclosing an area A, wherein the two-dimensional image data and three-dimensional OCT data are registered via a computer processor so that the tissue abnormality is identified in the three-dimensional OCT data by the boundary drawn on the two-dimensional image and displayed on a computer screen;
        iv) calculating the volume v within the boundary and between the first segment and the second segment;
        v) calculating the average thickness t between the first segment and the second segment along the boundary; and
        vi) calculating the volume of the region of interest $V=v-(t\times A)$; and
    b) administering a treatment to the subject based on the area and/or the volume of the tissue abnormality.

2. The method of claim 1 wherein the patient has macular degeneration and the tissue abnormality is a central neovascularization lesion complex.

3. The method of claim 1 wherein the treatment comprises administering to the subject an agent targeting vascular endothelial growth factor and/or an agent targeting platelet derived growth factor.

4. The method of claim 1 wherein the boundary is a circle, ellipse, polygon, or irregular shape.

5. The method of claim 1 further comprising determining a greatest linear distance across the tissue abnormality in the two-dimensional image data.

6. The method of claim 1 wherein the boundary is a continuous boundary or a discontinuous boundary comprising one or more points, dots, straight line segments, or curved line segments marking the edges of the tissue abnormality.

7. The method of claim 1 wherein the three-dimensional OCT data is a three-dimensional OCT image.

8. The method of claim 1 wherein the two-dimensional image data is OCT fundus data, a two-dimensional image produced by integrating three-dimensional OCT data, a cross-sectional slice of three-dimensional OCT data, or a photograph.

9. The method of claim 1 wherein the area A is calculated by interpolating between a plurality of points indicating the boundary of the tissue abnormality.

10. The method of claim 1 wherein a user draws the boundary around the region of interest or draws a plurality of points indicating the boundary around the tissue abnormality.

11. The method of claim 1 wherein a user draws the boundary around the region of interest or draws a plurality of points indicating the boundary around the tissue abnormality using a computer input device.

12. The method of claim 1 wherein a user draws the boundary around the tissue abnormality or draws a plurality of points indicating the boundary around the tissue abnormality using a mouse, touchscreen, trackball, joystick, trackpad, stylus, or light pen.

13. The method of claim 1 wherein automated image processing draws the boundary around the tissue abnormality.

14. The method of claim 1 wherein the boundary is provided on normal biological tissue.

15. The method of claim 1 wherein the tissue abnormality is a lesion in the biological tissue.

16. The method of claim 1 wherein the biological tissue is retinal tissue and the tissue abnormality is a retinal lesion.

17. A method of identifying that a treatment of a subject having a tissue abnormality is successful, the method comprising:
   a) calculating a first area and/or a first volume of the tissue abnormality by:
      i) acquiring three-dimensional OCT data comprising at least a first segment and a second segment comprising the tissue abnormality;
      ii) acquiring two-dimensional image data comprising the tissue abnormality, wherein the tissue abnormality in the three-dimensional OCT data corresponds to the tissue abnormality in the two-dimensional data;
      iii) drawing a boundary around the tissue abnormality in the two-dimensional image data, the boundary enclosing an area A, wherein the two-dimensional image data and three-dimensional OCT data are registered via a computer processor so that the tissue abnormality is identified in the three-dimensional OCT data by the boundary drawn on the two-dimensional image and displayed on a computer screen;
      iv) calculating the volume v within the boundary and between the first segment and the second segment;
      v) calculating the average thickness t between the first segment and the second segment along the boundary;
      vi) calculating the volume of the region of interest $V=v-(t \times A)$;
   b) administering a treatment to the subject;
   c) calculating a second area and/or a second volume of the tissue abnormality by repeating step (a); and
   d) identifying the treatment of the patient as effective when the second area and/or the second volume of the tissue abnormality is less than the first area and/or the first volume of the tissue abnormality.

18. The method of claim 17 wherein the patient has macular degeneration and the tissue abnormality is a central neovascularization lesion complex.

19. The method of claim 17 wherein the treatment comprises administering to the subject an agent targeting vascular endothelial growth factor and/or an agent targeting platelet derived growth factor.

20. The method of claim 17 wherein the boundary is a circle, ellipse, polygon, or irregular shape.

21. The method of claim 17 further comprising determining a greatest linear distance across the tissue abnormality in the two-dimensional image data.

22. The method of claim 17 wherein the boundary is a continuous boundary or a discontinuous boundary comprising one or more points, dots, straight line segments, or curved line segments marking the edges of the tissue abnormality.

23. The method of claim 17 wherein the three-dimensional OCT data is a three-dimensional OCT image.

24. The method of claim 17 wherein the two-dimensional image data is OCT fundus data, a two-dimensional image produced by integrating three-dimensional OCT data, a cross-sectional slice of three-dimensional OCT data, or a photograph.

25. The method of claim 17 wherein the area A is calculated by interpolating between a plurality of points indicating the boundary of the tissue abnormality.

26. The method of claim 17 wherein a user draws the boundary around the region of interest or draws a plurality of points indicating the boundary around the tissue abnormality.

27. The method of claim 17 wherein a user draws the boundary around the region of interest or draws a plurality of points indicating the boundary around the tissue abnormality using a computer input device.

28. The method of claim 17 wherein a user draws the boundary around the tissue abnormality or draws a plurality of points indicating the boundary around the tissue abnormality using a mouse, touchscreen, trackball, joystick, trackpad, stylus, or light pen.

29. The method of claim 17 wherein automated image processing draws the boundary around the tissue abnormality.

30. The method of claim 17 wherein the boundary is provided on normal biological tissue.

31. The method of claim 17 wherein the tissue abnormality is a lesion in the biological tissue.

32. The method of claim 17 wherein the biological tissue is retinal tissue and the tissue abnormality is a retinal lesion.

* * * * *